US007340945B2

United States Patent
Tashiro

(10) Patent No.: US 7,340,945 B2
(45) Date of Patent: Mar. 11, 2008

(54) FAILURE DETECTION APPARATUS AND FAILURE DETECTION METHOD FOR EXHAUST GAS SENSOR

(75) Inventor: Kenji Tashiro, Toyota (JP)

(73) Assignee: Toyota Jidosha Kabushiki Kaisha, Toyota-shi (JP)

( * ) Notice: Subject to any disclaimer, the term of this patent is extended or adjusted under 35 U.S.C. 154(b) by 2 days.

(21) Appl. No.: 11/499,778

(22) Filed: Aug. 7, 2006

(65) Prior Publication Data

US 2007/0045112 A1    Mar. 1, 2007

(30) Foreign Application Priority Data

Sep. 1, 2005    (JP)    ............................. 2005-253359

(51) Int. Cl.
*G01M 19/00*    (2006.01)
(52) U.S. Cl. ..................................... 73/119 R; 73/1.06
(58) Field of Classification Search ................. 73/1.01, 73/1.02, 1.03, 1.06, 1.07, 23.31, 23.32, 116, 73/117.2, 117.3, 118.1, 119 R
See application file for complete search history.

(56) References Cited

U.S. PATENT DOCUMENTS

| | | | | |
|---|---|---|---|---|
| 6,662,638 | B2 * | 12/2003 | Surnilla | 73/118.1 |
| 6,711,932 | B2 | 3/2004 | Iwazaki et al. | |
| 6,920,751 | B2 * | 7/2005 | Yasui et al. | 60/277 |
| 6,961,653 | B2 * | 11/2005 | Maki | 701/109 |
| 6,976,382 | B2 * | 12/2005 | Kadowaki et al. | 73/1.06 |
| 7,021,300 | B2 * | 4/2006 | Maki et al. | 123/688 |
| 2003/0097873 | A1 * | 5/2003 | Surnilla | 73/118.1 |
| 2005/0005690 | A1 * | 1/2005 | Maki | 73/118.1 |
| 2005/0061067 | A1 * | 3/2005 | Maki et al. | 73/118.1 |
| 2006/0277971 | A1 * | 12/2006 | Tashiro et al. | 73/1.06 |
| 2007/0010932 | A1 * | 1/2007 | Gotoh et al. | 701/114 |

FOREIGN PATENT DOCUMENTS

| | | |
|---|---|---|
| JP | 8-21282 | 1/1996 |
| JP | 8-327586 | 12/1996 |
| JP | 2003-14683 | 1/2003 |
| JP | 2003-20989 | 1/2003 |

* cited by examiner

*Primary Examiner*—Eric S. McCall
(74) *Attorney, Agent, or Firm*—Kenyon & Kenyon LLP

(57) ABSTRACT

An air-fuel ratio sensor has an exhaust-side electrode and an atmosphere-side electrode. The atmosphere-side electrode is disposed in an atmosphere layer that communicates with the atmosphere. Since the air-fuel ratio sensor is disposed in an exhaust passage, exhaust gas enters the atmosphere layer if a sensor crack occurs. Ordinarily, forward voltage is applied to the air-fuel ratio sensor to obtain an output thereof in accordance with the air-fuel ratio. Immediately after the applied voltage is switched to reverse voltage, sensor current i1 in accordance with the impedance flows, regardless of the presence/absence of a sensor crack. After that, the sensor current converges to a value i2 that is in accordance with the oxygen concentration in the atmosphere layer. The presence/absence of a sensor crack is determined by comparing the value obtained by correcting i2 by i1, with a criterion value.

17 Claims, 24 Drawing Sheets

FIG. 4A
FIG. 4B
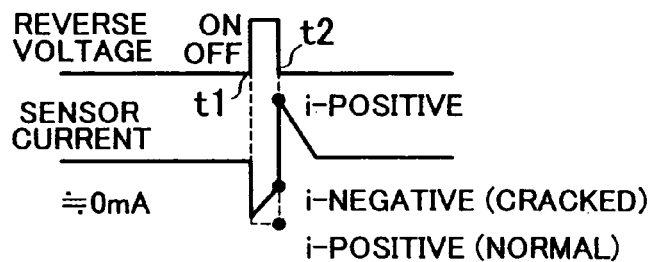
FIG. 5
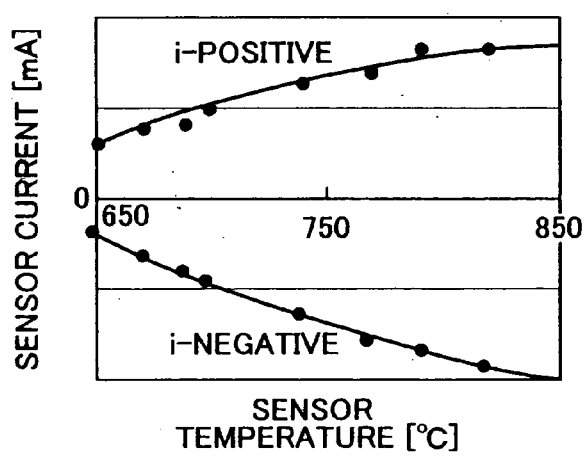

FIG. 9A  F/C
FIG. 9B  APPLIED VOLTAGE
FIG. 9C  ATMOSPHERE LAYER O2 CONCENTRATION
FIG. 9D  SENSOR VOLTAGE
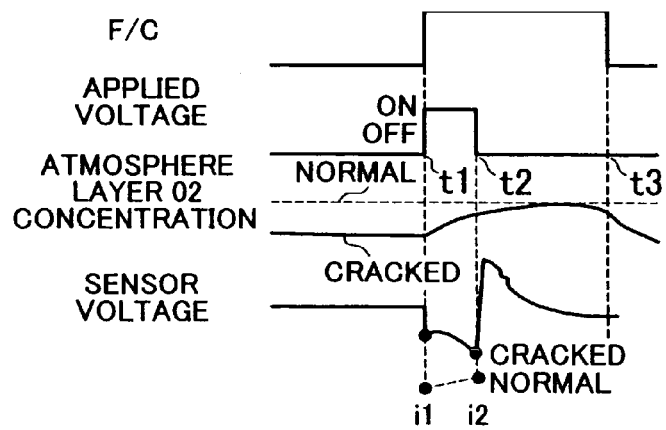
FIG. 10A
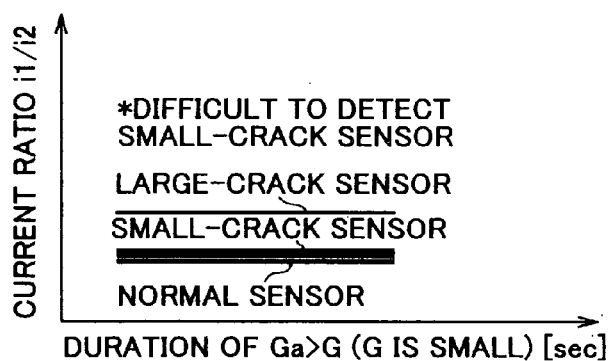
FIG. 10B
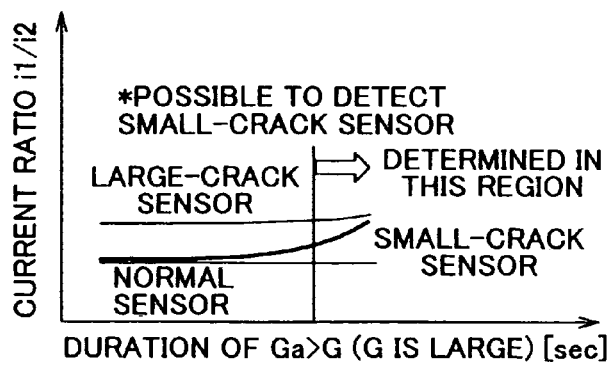

FIG. 13A
FIG. 13B
FIG. 13C
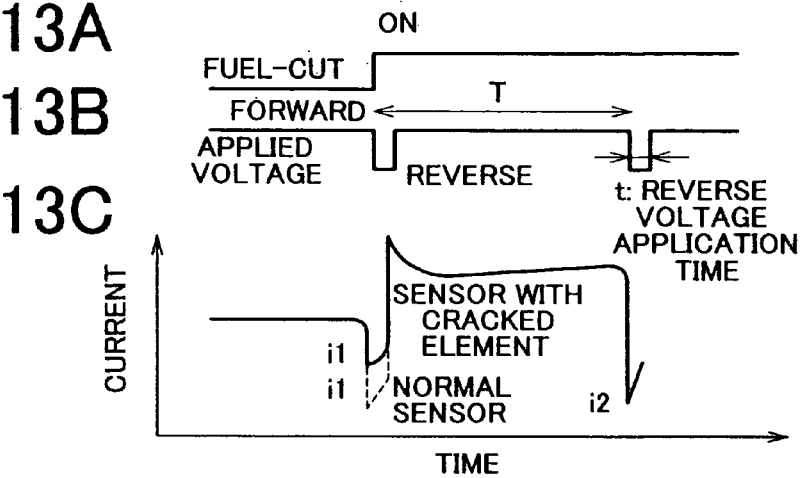
FIG. 14A
FIG. 14B
FIG. 14C
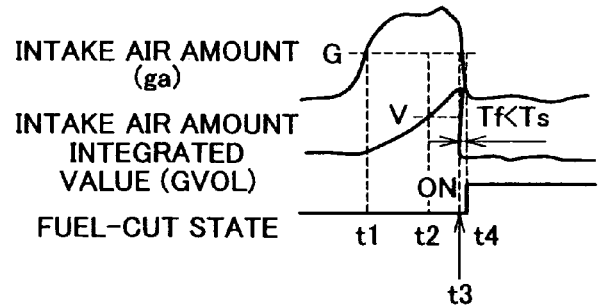
FIG. 15A
FIG. 15B
FIG. 15C
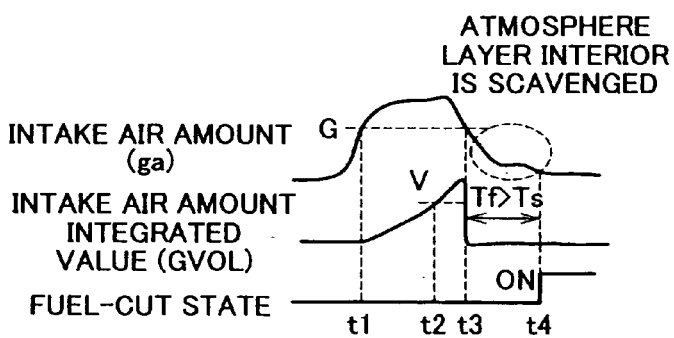

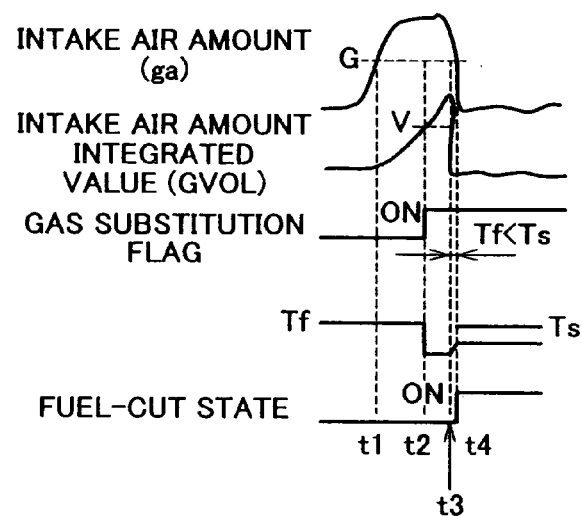

FAILURE DETECTION APPARATUS AND FAILURE DETECTION METHOD FOR EXHAUST GAS SENSOR

INCORPORATION BY REFERENCE

The disclosure of Japanese Patent Application No. 2005-253359 filed on Sep. 1, 2005, including the specification, drawings and abstract is incorporated herein by reference in its entirety.

BACKGROUND OF THE INVENTION

1. Field of Invention

This invention relates to a failure detection apparatus and a failure detection method for an exhaust gas sensor and, more particularly, to a failure detection apparatus for an exhaust gas that detects cracks in the exhaust gas sensor, and a method for detecting a failure in the exhaust gas sensor.

2. Description of Related Art

One system for detecting abnormalities in an oxygen sensor disposed in the exhaust passage of an internal combustion engine is described in Japanese Patent Application Publication No. JP-A-HEI-08-327586. The reference describes an oxygen sensor with exhaust-side electrode that is exposed to exhaust gas, and an atmosphere-side electrode that is exposed to an atmosphere layer within a sensor element thereof.

The atmosphere layer is a space that is separated from the interior of the exhaust passage by the sensor element. In addition, the atmosphere layer communicates with the atmosphere. The described system applies a voltage between the atmosphere-side electrode and the exhaust-side electrode, and then determines whether an abnormality is present based on the magnitude of the electric current that flows between the electrodes.

In the described system, the exhaust-side electrode serves as a positive electrode and with the atmosphere-side electrode serves as a negative electrode. When a voltage is applied between the two electrodes, an electric current corresponding to the oxygen concentration in the atmosphere layer flows through the sensor element. That is, if the sensor element is normal, the electric current corresponding to the oxygen concentration in the atmosphere (hereinafter, referred to as "normal electric current") flows. On the other hand, if there is a crack in the sensor element and exhaust gas enters the atmosphere layer, the oxygen concentration in the atmosphere layer is decreased, which results in a decrease in the electric current that flows through the sensor element relative to the normal electric current.

Thus, the value of the electric current that is generated by applying voltage between the exhaust-side electrode and the atmosphere-side electrode changes in accordance with whether or not there is a crack in the sensor element. Therefore, by focusing attention on the value of the electric current, it is possible to determine whether or not there is a crack in the sensor element.

However, the magnitude of the electric current that flows through the sensor element changes in accordance with the impedance of the sensor element. The temperature of the sensor element affects the impedance of the sensor element. Therefore, unless the temperature of the sensor element is accurately detected, it is difficult to correctly determine whether an abnormality is present in the sensor element based on the electric current that flows through the sensor element. In this respect, the above-described system is not necessarily capable of correctly detecting a the presence of a crack in the sensor element at all times.

SUMMARY OF THE INVENTION

The invention provides a failure detection apparatus and a failure detection method for an exhaust gas sensor that are capable of correctly detecting a crack of a sensor element at all times without being affected by differences in the impedance of the sensor element.

A first aspect of the invention is a failure detection apparatus for an exhaust gas sensor that has an exhaust-side electrode exposed in the exhaust passage of an internal combustion engine, an atmosphere layer forming member that forms an atmosphere layer in the interior of the exhaust passage, an atmosphere-side electrode exposed to the atmosphere layer, and an electrolyte layer that is disposed between the exhaust-side electrode and the atmosphere-side electrode and that allows movement of oxygen ions between the exhaust-side electrode and the atmosphere-side electrode. The failure detection apparatus comprises: a reverse voltage application device that applies a reverse voltage between the atmosphere-side electrode and the exhaust-side electrode so that the electric potential of the exhaust-side electrode becomes higher than the electric potential of the atmosphere-side electrode; a reverse current detection device that detects the value of the reverse electric current that flows between the atmosphere-side electrode and the exhaust-side electrode in association with the application of the reverse voltage; an impedance correlation value acquisition device that acquires an impedance correlation value that correlates with the impedance between the atmosphere-side electrode and the exhaust-side electrode; and a failure detection portion that detects a failure in the exhaust gas sensor by comparing the value of reverse current and a criterion value while filtering out the influence of the impedance superposed on the value of reverse current.

The failure detection portion may detect a failure in the exhaust gas sensor by comparing a corrected value of the reverse current, which is obtained by correcting the value of the reverse electric current by the impedance correlation value with the criterion value. By using the corrected value of the reverse current the influence of the impedance superposed on the value of reverse electric current is filtered out.

Therefore, by correcting the value of the reverse current by the impedance correlation value, a corrected reverse current value is computed. The reverse electric current value is determined by the oxygen concentration in the atmosphere and the impedance of the sensor element. If the value is corrected by the impedance correlation value, a value that correctly represents the oxygen concentration in the atmosphere layer is determined. According to this aspect, by comparing the corrected reverse current with the criterion value, a crack in the exhaust gas sensor can be correctly detected at all times, regardless of the impedance of the sensor element.

The failure detection portion may detect a failure in the exhaust gas sensor by obtaining a corrected value of the criterion value by superposing on the criterion value the influence of the impedance superposed on the value of reverse current, and by comparing the value of reverse current and the corrected criterion value.

Therefore, the presence/absence of a failure is determined based on the comparison of the corrected criterion value and the value of reverse current. The influence of the oxygen concentration in the atmosphere layer and the impedance of the sensor element are superposed on the value of reverse current. The corrected criterion value is obtained by superposing the influence of the impedance of the sensor element on the criterion value. Therefore, on the basis of the comparison therebetween, a crack of the exhaust gas sensor can be accurately detected at all times regardless of the impedance of the sensor element.

The failure detection portion may detect a failure based on the value of reverse current measured after the reverse voltage has been applied for a predetermined period of time.

Therefore, a failure is detected on the basis of the value of reverse current measured at when a predetermined period of time has elapsed after the reverse has been applied. Since the elapse of the predetermined period of time is awaited, the value of reverse current approaches a convergence value. Therefore, according to this aspect, stable failure detection can be performed.

The failure detection portion may compare the value of reverse current measured when a predetermined period of time has elapsed after the reverse voltage has been applied, with the criterion value.

Therefore, the reverse measured after the reverse voltage has been applied for a predetermined period of time is compared with the criterion value. Since the elapse of the predetermined time is awaited, the value of reverse current approaches a convergence value. Therefore, according to this aspect, stable failure detection can be performed.

The impedance correlation value may be the value of reverse current that occurs when the reverse voltage is applied.

Therefore, the value of reverse current measured after the reverse voltage is applied is set as the impedance correlation value. Immediately after the application of the reverse voltage, oxygen is sufficiently present near the atmosphere-side electrode. Therefore, the reverse voltage that occurs at that time point is not restricted by the oxygen concentration in the atmosphere layer, but assumes a value that is in accordance with the impedance value of the sensor element. Therefore, according to the embodiment, the failure detection can be accurately performed.

Furthermore, the failure detection apparatus for the exhaust gas sensor may comprise a forward voltage application device that applies a forward voltage between the exhaust-side electrode and the atmosphere-side electrode so that the electric potential of the exhaust-side electrode becomes higher than the electric potential of the atmosphere-side electrode. In addition, the impedance correlation value may be a value of the forward electric current that flows between the exhaust-side electrode and the atmosphere-side electrode when the voltage applied between the atmosphere-side electrode and the exhaust-side electrode is changed from the reverse voltage to the forward voltage.

Therefore, the value of forward electric current that occurs when the reverse voltage is changed to the forward voltage is set as the impedance correlation value. Immediately after the change to the forward voltage, oxygen is sufficiently present near the exhaust-side electrode. Hence, the forward voltage that occurs at that time point is not restricted by the oxygen concentration in exhaust gas, but assumes a value that is in accordance with the value of impedance of the sensor element. Hence, according to this aspect, the failure detection can be accurately performed.

The failure detection apparatus for the exhaust gas sensor may further comprise an exhaust pressure determination device that determines whether or not an exhaust pressure exceeds a reference value, and an execution condition determination device that permits detection of the failure only when a period during which the exhaust pressure exceeds the reference value exceeds a criterion period.

Therefore, it is possible to permit the detection of a failure only in the case where the period during which the exhaust pressure exceeds the reference value exceeds the predetermined period. In the case where the exhaust pressure is low, exhaust gas does not enter the atmosphere even if there is a crack in the sensor element. If exhaust gas has not entered the atmosphere layer, the influence of a crack will not appear on the value of reverse electric current, and therefore correct failure detection cannot be performed. According to this aspect, it is possible to permit the failure detection only under an environment where if there is a crack, exhaust gas enters the atmosphere layer. Hence, it is possible to improve the accuracy of the failure detection.

The failure detection apparatus for the exhaust gas sensor may further comprise a fuel-cut device that performs a fuel-cut if an engine speed reaches a permissible upper limit value, and an execution prohibition device that prohibits detection of the failure during execution of the fuel-cut.

Therefore, if the fuel-cut is performed in order to prevent overspeed of the internal combustion engine, the failure detection can be prohibited. Under an environment where the fuel-cut operates to prevent engine overspeed, gas in the exhaust passage enters the atmosphere layer if the atmosphere layer has a crack and the exhaust pressure is sufficiently high. During the fuel-cut, the gas is atmospheric air, so that the atmosphere layer is scavenged; therefore, the influence of a crack will not appear in the reverse electric current. According to this aspect, it is possible to effectively avoid making a false determination of normality under such an environment.

The failure detection apparatus for the exhaust gas sensor may further comprise a temperature acquisition device that acquires a temperature of the exhaust gas sensor, and an execution prohibition device that prohibits detection of the failure if the temperature of the exhaust gas sensor has not reached an execution permission temperature.

Therefore, in the case where the temperature of the exhaust gas sensor has not reached the execution permission temperature, the failure detection can be prohibited. Under an environment where the temperature of the exhaust gas sensor is low, a difference in the oxygen concentration in the atmosphere layer may sometimes not be properly reflected in the relationship between the reverse electric current and the impedance correlation value. According to this aspect, it is possible to effectively prevent false failure detection from being made under such an environment.

The failure detection apparatus for the exhaust gas sensor may further comprise a temperature acquisition device that acquires a temperature of the exhaust gas sensor, and a predetermined time setting device that sets the predetermined time longer if the temperature of the exhaust gas sensor is higher.

Therefore, the time until the value of reverse electric current is acquired can be set longer if the temperature of the exhaust gas sensor is higher. In a region of low temperatures, as the aforementioned time is longer, the relationship between the value of reverse electric current and the impedance correlation value at the time of the normal condition more closely approaches the relationship therebetween exhibited at the time of occurrence of a crack in the sensor. Therefore, under a low temperature environment, it is advisable not to set the aforementioned time long. On the other hand, after the temperature has sufficiently risen, the relationship between the value of reverse electric current and the impedance correlation value at the time of the normal condition does not so closely approach the relation therebetween exhibited at the time of occurrence of a crack even if the aforementioned time is set long. The influence of occurrence of a crack appears in the reverse electric current to a greater extent if the aforementioned time is longer. Therefore, under a high temperature environment, the longer the aforementioned time, the easier the discrimination between the normal condition and the abnormal condition. According to this aspect, by changing the stabilization time in accordance with the temperature of the exhaust gas sensor, sufficiently high accuracy of the failure detection can be maintained over a wide region of temperature.

A second aspect of the invention is a failure detection apparatus for an exhaust gas sensor that has an exhaust-side electrode exposed in an exhaust passage of an internal combustion engine, an atmosphere layer forming member that forms an atmosphere layer in an interior of the exhaust passage, an atmosphere-side electrode exposed to the atmosphere layer, and an electrolyte layer that is disposed between the exhaust-side electrode and the atmosphere-side electrode and that allows movement of oxygen ions between the exhaust-side electrode and the atmosphere-side electrode. The failure detection apparatus comprises: a fuel-cut device that executes a fuel-cut when a fuel-cut condition is satisfied; a reverse voltage application device that applies a reverse voltage between the atmosphere-side electrode and the exhaust-side electrode so that an electric potential of the exhaust-side electrode becomes higher than an electric potential of the atmosphere-side electrode; a reverse current detection device that detects a value of reverse current that flows between the atmosphere-side electrode and the exhaust-side electrode in association with application of the reverse voltage; a failure detection portion that detects the value of reverse current when the fuel-cut begins, and that detects the value of reverse current at a time point when the fuel-cut has continued for a predetermined time, and that detects a failure in the exhaust gas sensor based on those values of reverse current; an exhaust pressure determination device that determines whether or not an exhaust pressure exceeds a reference value; a filling condition determination device that determines that an exhaust gas filling condition is satisfied if a period during which the exhaust pressure exceeds the reference value exceeds a criterion period; a filling condition maintenance device that maintains holding of the exhaust gas filling condition only during a period that begins after the exhaust pressure becomes lower than the reference value and that ends when a filling maintenance time elapses; and an execution condition determination device that permits detection of the failure only if the holding of the filling condition is recognized at a time point when the fuel-cut begins.

According to the second aspect, after the fuel-cut begins, the measurement of the reverse current is performed. If there is a crack in the sensor, exhaust gas can enter the atmosphere layer before the fuel-cut begins. Then, as the fuel-cut begins and air begins to flow through the exhaust passage, the interior of the atmosphere layer is scavenged and the exhaust gas therein is discharged. The value of reverse current, which has a correlation with the oxygen concentration in the atmosphere layer, increases as the exhaust gas in the atmosphere layer is scavenged. Therefore, if sufficient exhaust gas has entered the atmosphere layer when the fuel-cut begins, it is possible to determine whether a crack is present on the basis of the subsequent behavior of the reverse current, no matter what value the impedance of the exhaust gas sensor assumes. While the exhaust gas filling condition has held and the holding of the condition is maintained, it can be assured that sufficient exhaust gas is present in the atmosphere layer. In the invention, it is possible to permit execution of the failure detection only in the case where this assurance is obtained. Therefore, according to this aspect, it is possible to accurately perform the failure diagnostic of the exhaust gas sensor without being affected by the impedance.

A third aspect of the invention is a failure detection method for an exhaust gas sensor that has an exhaust-side electrode exposed in an exhaust passage of an internal combustion engine, an atmosphere layer forming member that forms an atmosphere layer in an interior of the exhaust passage, an atmosphere-side electrode exposed to the atmosphere layer, and an electrolyte layer that is disposed between the exhaust-side electrode and the atmosphere-side electrode and that allows movement of oxygen ions between the exhaust-side electrode and the atmosphere-side electrode. The failure detection method comprises: applying a reverse voltage between the atmosphere-side electrode and the exhaust-side electrode so that an electric potential of the exhaust-side electrode becomes higher than an electric potential of the atmosphere-side electrode; detecting a value of reverse current that flows between the atmosphere-side electrode and the exhaust-side electrode in association with application of the reverse voltage; acquiring an impedance correlation value that has a correlation with an impedance between the atmosphere-side electrode and the exhaust-side electrode; and detecting a failure of the exhaust gas sensor by comparing the value of reverse current and a criterion value while taking into account an influence of the impedance superposed on the value of reverse current.

A fourth aspect of the invention is a failure detection method for an exhaust gas sensor that has an exhaust-side electrode exposed in an exhaust passage of an internal combustion engine, an atmosphere layer forming member that forms an atmosphere layer in an interior of the exhaust passage, an atmosphere-side electrode exposed to the atmosphere layer, and an electrolyte layer that is disposed between the exhaust-side electrode and the atmosphere-side electrode and that allows movement of oxygen ions between the exhaust-side electrode and the atmosphere-side electrode. The failure detection method comprises: executing a fuel-cut when a fuel-cut condition is satisfied; applying a reverse voltage between the atmosphere-side electrode and the exhaust-side electrode so that an electric potential of the exhaust-side electrode becomes higher than an electric potential of the atmosphere-side electrode; detecting a value of reverse current that flows between the atmosphere-side electrode and the exhaust-side electrode in association with application of the reverse voltage; detecting the value of reverse current when the fuel-cut begins, and detecting the value of reverse current at a time point when the fuel-cut has continued for a predetermined time, and detecting a failure in the exhaust gas sensor based on those values of reverse current; determining whether or not an exhaust pressure exceeds a reference value; determining that an exhaust gas filling condition is satisfied if a period during which the exhaust pressure exceeds the reference value exceeds a criterion period; maintaining holding of the exhaust gas filling condition only during a period that begins after the exhaust pressure becomes lower than the reference value and that ends when a filling maintenance time elapses; and permitting detection of the failure only if the holding of the filling condition is recognized at a time point when the fuel-cut begins.

BRIEF DESCRIPTION OF THE DRAWINGS

The foregoing and further objects, features and advantages of the invention will become apparent from the following description of preferred embodiments with reference to the accompanying drawings, wherein like numerals are used to represent like elements and wherein:

FIGS. 4A and 4B are timing charts for describing a technique used in the first embodiment to determine the presence/absence of a sensor crack;

FIG. 5 is a diagram for describing the temperature characteristic of the sensor current (i-negative) generated in association with application of the reverse voltage, and the temperature characteristic of the sensor current (i-positive) that occurs immediately following the reversal to a forward voltage;

FIGS. 9A, 9B, 9C and 9D are timing charts for describing a technique used to determine the presence/absence of a sensor crack in a modification of the second embodiment;

FIGS. 10A and 10B are diagrams for describing the influence exerted on an electric current ratio (i1/i2) by the size of the criterion value G that is compared with the amount of intake air Ga;

FIGS. 13A, 13B and 13C timing charts for describing a technique used to determine the presence/absence of a sensor crack in a fifth embodiment of the invention;

FIGS. 14A, 14B and 14C are timing charts for describing an operation in which if there is a sensor crack, exhaust gas remains in an atmosphere layer when the fuel-cut begins;

FIGS. 15A, 15B and 15C are timing charts for describing an operation in which even if there is a sensor crack, exhaust gas does not remain in the atmosphere layer when the fuel-cut begins;

FIGS. 16A, 16B, 16C, 16D and 16E are timing charts for describing an operation performed in the case where the sensor crack detection is permitted in the fifth embodiment;

DETAILED DESCRIPTION OF THE PREFERRED EMBODIMENTS

Figure 1:
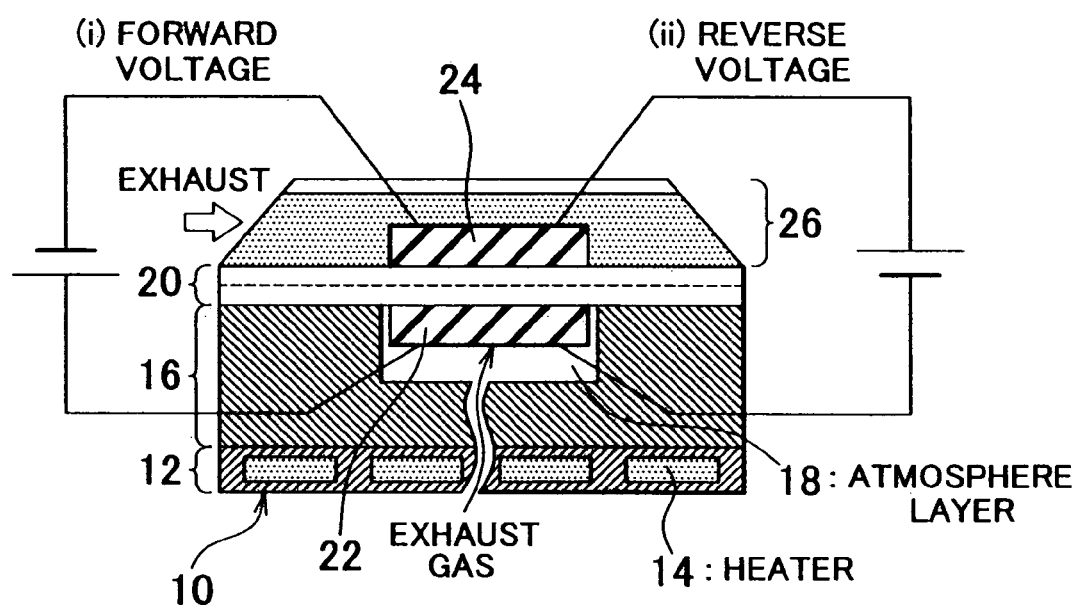
FIG. 1 is a diagram for describing the construction of an air-fuel ratio sensor used in a first embodiment of the invention.

FIG. 1 shows the construction of an air-fuel ratio sensor 10 according to a first embodiment of the invention. More specifically, FIG. 1 shows the sectional view of the sensor element portion of the air-fuel ratio sensor 10. The air-fuel ratio sensor 10 includes a sensor element that has the sectional structure shown in FIG. 1, and a cover that protects the sensor element. The air-fuel ratio sensor 10 is attached to the exhaust passage of an internal combustion engine so that the sensor element covered by the cover is exposed to exhaust gas.

The cover of the air-fuel ratio sensor 10 has a plurality of vent holes so that the gas flowing through the exhaust passage reaches the sensor element. Thus, the periphery of the air-fuel ratio sensor 10 (sensor element) is exposed to exhaust gas.

The air-fuel ratio sensor 10 has a heater layer 12. A heater 14 for heating the sensor element to an activation temperature is embedded within the heater layer 12. In FIG. 1, an atmosphere layer forming member 16 is disposed on the heater layer 12. The atmosphere layer forming member 16 may be formed from ceramics such as alumina and the like.

In FIG. 1, an electrolyte layer 20 is disposed on the upper portion of the atmosphere layer forming member 16. The electrolyte layer 20 may be formed from zirconia or the like. The central upper portion of the atmosphere layer forming member 16 has a recess for forming an atmosphere layer 18. The atmosphere layer 18 is segregated from an interior space of the exhaust passage by the atmosphere layer forming member 16 and the electrolyte layer 20, and is open to the atmosphere through an atmospheric hole (not shown).

In FIG. 1, an atmosphere-side electrode 22 is disposed on a lower surface of the electrolyte layer 20 so that the atmosphere-side electrode 22 is exposed to the atmosphere layer 18. On the other hand, an upper surface of the electrolyte layer 20 is provided with an exhaust-side electrode 24. The exhaust-side electrode 24 is covered by a diffusion resistance layer 26. The diffusion resistance layer 26 is a layer of a porous material. The diffusion resistance layer 26 has a function of moderately restricting the speed at which the gas flowing in the exhaust passage reaches the exhaust-side electrode 24.

A forward voltage denoted by a character (i) and a reverse voltage denoted by a character (ii) are selectively applied to the air-fuel ratio sensor 10. Specifically, the forward voltage is applied so that the electric potential of the atmosphere-side electrode 22 becomes higher than that of the exhaust-side electrode 24. In this case, a sensor current that corresponds to the amount of excess or deficiency of oxygen in exhaust gas, that is, a sensor current that corresponds to the air-fuel ratio of exhaust gas, flows between the atmosphere-side electrode 22 and the exhaust-side electrode 24. Therefore, by detecting the sensor current, the exhaust air-fuel ratio can be detected. In the following description, the current that flows from the atmosphere-side electrode 22 toward the exhaust-side electrode 24 is termed "forward current", and the current flowing in the opposite direction is termed "reverse current". Incidentally, in the present specification, the term "forward current" or "reverse current" sometimes mean "value of the forward current" or "value of the reverse current".

Specifically, the reverse voltage is applied so that the electric potential of the exhaust-side electrode 24 becomes higher than that of the atmosphere-side electrode 22. In this case, the oxygen in contact with the surface of the atmosphere-side electrode 22 becomes ionized and is pumped toward the exhaust-side electrode 24. As a result, the reverse current in accordance with the amount of oxygen pumped from the atmosphere layer 18 flows between the atmosphere-side electrode 22 and the exhaust-side electrode 24.

Figure 2:
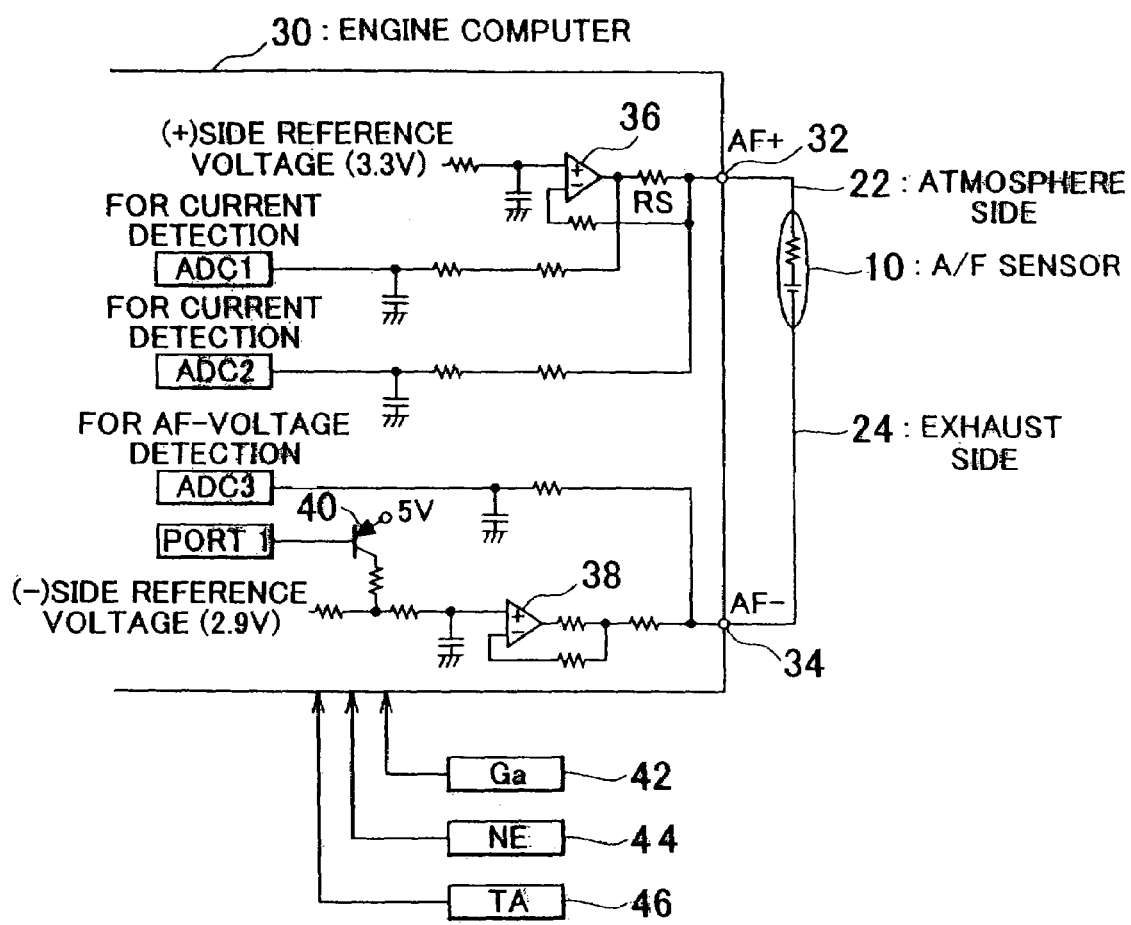
FIG. 2 is a circuit diagram for describing the construction of an engine computer for driving the air-fuel ratio sensor shown in FIG. 1.

FIG. 2 is a circuit diagram for describing the construction of an engine computer 30 that drives the air-fuel ratio sensor 10. The circuit shown in FIG. 2 includes a positive electrode terminal 32 connected to the atmosphere-side electrode 22 of the air-fuel ratio sensor 10, and a negative electrode terminal 34 connected to the exhaust-side electrode 24 of the air-fuel ratio sensor 10.

The electric potential of the positive electrode terminal 32 is always controlled to a positive reference voltage (3.3 V) by feedback via an operational amplifier 36. A feedback circuit employing an operational amplifier 38, and a switch circuit employing a transistor 40 are connected to the negative electrode terminal 34. The transistor 40 switches between an on and an off in accordance with the state of a port 1. The electric potential of the negative electrode terminal 34, when the transistor 40 is off, is controlled to a negative reference voltage (2.9 V) by a function of the operational amplifier 38. On the other hand, when the transistor 40 is turned on, the input voltage to the operational amplifier 38 increases so that the electric potential of the negative electrode terminal 34 rises to a reverse voltage (about 3.7 V) that is higher than the positive reference voltage.

Sensors, such as an air flow meter 42, a rotational speed sensor 44, a throttle sensor 46, etc., are connected to the engine computer 30. The air flow meter 42 detects the amount of intake air Ga of the internal combustion engine. The rotational speed sensor 44 outputs a signal in accordance with the engine rotation speed NE. The throttle sensor 46 outputs a signal in accordance with the degree of throttle opening TA.

With the construction as described above, the engine computer 30 is able to apply a forward voltage of about 0.4 V to the air-fuel ratio sensor 10 by turning the port 1 off. Furthermore, the engine computer 30 is able to apply a reverse voltage of about 0.4 V to the air-fuel ratio sensor 10 by turning the port 1 on.

The engine computer 30 also has an ADC1 port, an ADC2 port, and an ADC3 port. An electric potential difference that is accordance with the sensor current that flows through the air-fuel ratio sensor 10 appears between the ADC1 port and ADC2 port. The electric potential of the negative electrode terminal 34 is led to the ADC3 port. Therefore, by taking in the electric potential of the ADC1 port and the electric potential of the ADC2 port, the engine computer 30 is detects the sensor current. Furthermore, by taking in the electric potential of the ACD3 port, the engine computer 30 detects the electric potential supplied to the exhaust-side electrode 24 of the air-fuel ratio sensor 10.

The engine computer 30 shown in FIG. 2 detects the sensor current while applying the forward voltage of about 0.4 V to the air-fuel ratio sensor 10. In this case, on the basis of the sensor current, it is possible to detect the exhaust air-fuel ratio. Furthermore, the engine computer 30 detects the sensor current (reverse current) while applying the reverse voltage of about 0.4 V to the air-fuel ratio sensor 10. In this case, the reverse current assumes a value that corresponds to the amount of oxygen pumped from the atmosphere layer 18.

The interior of the atmosphere layer 18 is kept separate from the interior of the exhaust passage, if the air-fuel ratio sensor 10 is normal. However, a crack connecting to the atmosphere layer 18 or the like sometimes occur in the air-fuel ratio sensor 10. FIG. 1 shows a state where a crack as mentioned above has occurred across the heater layer 12 and the atmosphere-layer forming member 16.

During operation of the internal combustion engine, the pressure of exhaust gas makes the internal pressure of the exhaust passage higher than the pressure in the atmosphere layer 18. Therefore, if there is a crack in the air-fuel ratio sensor 10, it is possible for the gas passing through the exhaust passage to enter the atmosphere layer 18 through the crack. In this case, the oxygen concentration in the atmosphere layer 18 becomes lower, due to the mixture of exhaust gas, than in the case where the aforementioned crack is absent.

The amount of oxygen pumped from the atmosphere layer 18 is likely to be smaller if the oxygen concentration in the atmosphere layer 18 is lower. Therefore, if there is a crack across the heater layer 12 and the atmosphere-layer forming member 16, the reverse current generated upon application of the reverse voltage is likely to assume a smaller value than during the normal state. That is, the reverse current generated upon application of the reverse voltage assumes different values depending on whether or not there is a crack in the air-fuel ratio sensor 10. Therefore, in the system of this embodiment, it is conceivable to determine whether or not there is a crack in the air-fuel ratio sensor 10 on the basis of the value of the reverse current.

Figure 3:
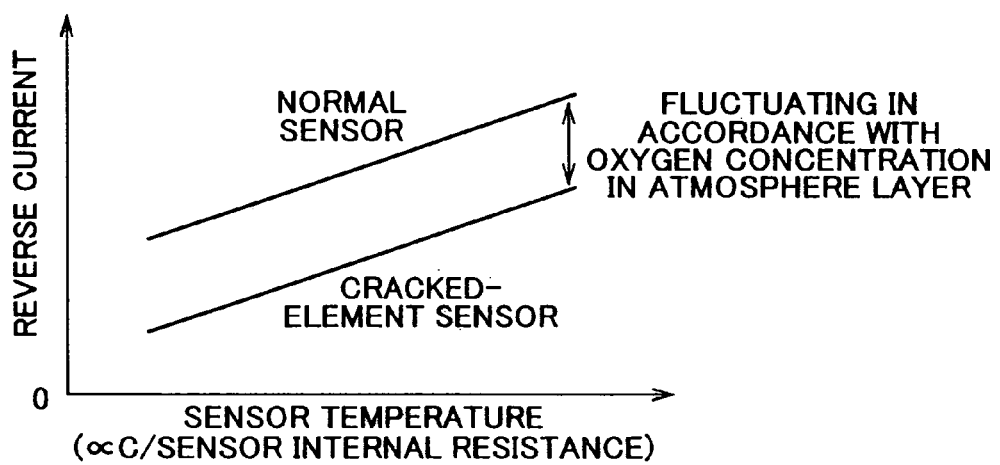
FIG. 3 is a diagram representing a relationship between a reverse current generated in a normal air-fuel ratio sensor and the sensor temperature thereof, and a relationship between the reverse current generated in a cracked air-fuel ratio sensor and the sensor temperature thereof.

However, the value of the reverse current changes in accordance with the impedance of the sensor element. The impedance of the air-fuel ratio sensor greatly changes in accordance with the sensor temperature. FIG. 3 is a diagram representing a relationship between the reverse current generated in the air-fuel ratio sensor 10 and the sensor temperature thereof when there is no abnormality present in the air-fuel ration sensor 10, and a relationship between the reverse electric current generated in the air-fuel ratio sensor 10 and the sensor temperature when there is a crack in the air-fuel ratio sensor 10.

As shown in FIG. 3, if there is a crack in the air-fuel ratio sensor 10, exhaust gas enters the atmosphere layer. As a result, the oxygen concentration in the atmosphere layer 18 drops, so that the reverse current becomes smaller than when the air-fuel ratio sensor 10 is normal. In either case, however, the value of the reverse current increases as the sensor temperature increases, that is, as the internal resistance of the sensor decreases.

As a result, in FIG. 3, there is an overlap between the range of the reverse current generated in a normal air-fuel ratio sensor 10 and the range of the reverse current generated in a cracked air-fuel ratio sensor 10. In this case, it is difficult to determine whether there is a crack in the air-fuel ratio sensor 10, from the value of the reverse current itself.

FIGS. 4A and 4B are timing charts for describing the technique used in the embodiment to determine whether there is a crack in the air-fuel ratio sensor 10. More specifically, FIG. 4A is a diagram showing the time at which the reverse current is applied to the air-fuel ratio sensor 10. FIG. 4B is a diagram showing the waveform of the sensor current that flows through the air-fuel ratio sensor 10.

FIG. 4A shows a state where the reverse voltage is applied to the air-fuel ratio sensor 10 during a time t1 to t2, and where during periods other than that, the forward voltage is applied to the air-fuel ratio sensor 10. It is assumed herein that the exhaust gas has substantially a stoichiometric air-fuel ratio, and that the sensor current generated at the time of application of the forward voltage is substantially zero.

During application of the forward voltage up to the time t1, oxygen ions in the pumping process exist in a path from the exhaust-side electrode 24 to the atmosphere-side electrode, and oxygen exits near the surface of the atmosphere-side electrode 22. If, from this state, the application voltage is changed to the reverse voltage, reverse electric current that is in accordance with the impedance of the air-fuel ratio sensor 10 flows between the atmosphere-side electrode 22 and the exhaust-side electrode 24.

If there is no crack, sufficient oxygen exists in the atmosphere layer 18. Therefore, when there is no crack, the absolute value of the reverse current does not considerably decrease between the time t1 to t2 as indicated by broken lines in FIG. 4B. However, if there is a sensor crack, exhaust gas enters the atmosphere layer 18 at the time t1. In this case, since the oxygen concentration further drops as the pumping of oxygen progresses, the absolute value of the reverse current exhibits a clear decrease following the time t1, as indicated by a solid line in FIG. 4B. As a result, during the normal state the reverse current at the time t2 assumes a value that corresponds to the impedance (hereinafter, referred to as "i-negative (normal)"). On the other hand, when there is a crack, the reverse electric current at the time t2 assumes a value that is smaller in absolute value than the i-negative (normal) (hereinafter, referred to as "i-negative (cracked)".

At the time t2, oxygen ions in the pumping process exist in the path from the exhaust-side electrode 24 to the atmosphere-side electrode 22 and, furthermore, pumped oxygen also exists near the surface of the exhaust-side electrode 24. If from this state, the applied voltage is changed to the forward voltage, forward electric current (hereinafter, referred to as "i-positive") that corresponds to the impedance of the air-fuel ratio sensor 10 flows between the atmosphere-side electrode 22 and the exhaust-side electrode 24.

However, the i-negative (cracked) is a value that is smaller in absolute value than the i-negative (normal). However, the value thereof changes in accordance with the impedance of the air-fuel ratio sensor 10, that is, in accordance with the sensor temperature. Therefore, it cannot be determined from the value of the reverse current at the time t2 whether the reverse current is the i-negative (normal) or the i-negative (cracked). On the other hand, the i-positive is a value that corresponds to the impedance of the air-fuel ratio sensor 10, regardless of the presence/absence of a crack.

That is, the absolute value of the i-negative at the time t2, and the absolute value of the i-positive immediately after the time t2 exhibit similar dependencies with respect to the sensor temperature (impedance) as shown in FIG. 5. Therefore, if the i-negative is corrected by the i-positive, it becomes possible to filter out the influence of the impedance from the i-negative. More specifically, for example, if the value of the electric current ratio "i-negative/i-positive" or "i-positive/i-negative" is found, it becomes possible to correctly compute a characteristic value that has a correlation with respect to the oxygen concentration in the atmosphere layer 18 at the time t2 that does not include the influence of the impedance. Therefore, in this embodiment, during operation of the internal combustion engine, the electric current ratio (i-positive/i-negative) is determined, and then the presence/absence of a sensor crack is determined on the basis of the electric current ratio (i-positive/i-negative).

Figure 6A:
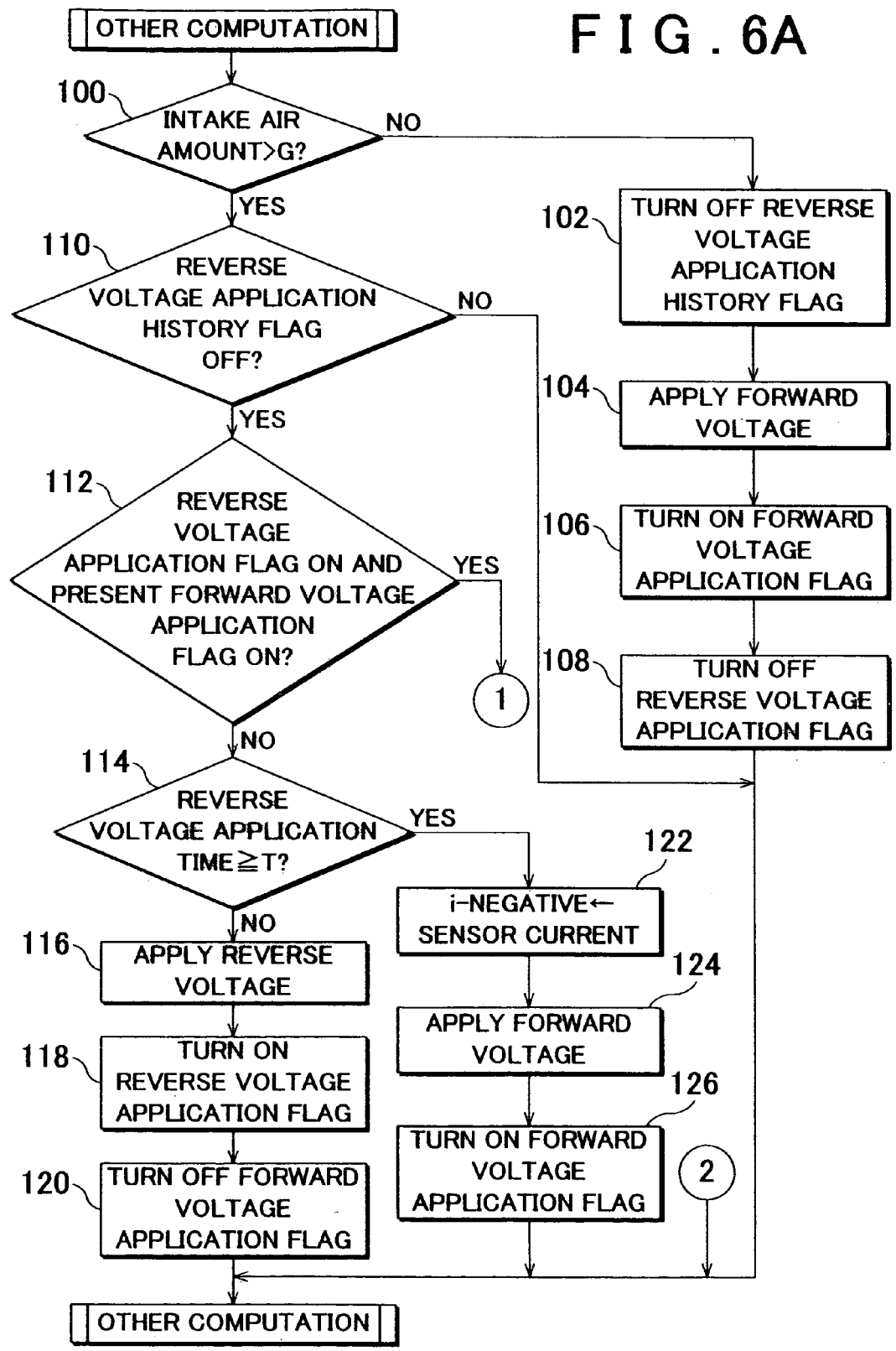
FIGS. 6A and 6B are flowcharts of a routine executed in the first embodiment.
Figure 6B:
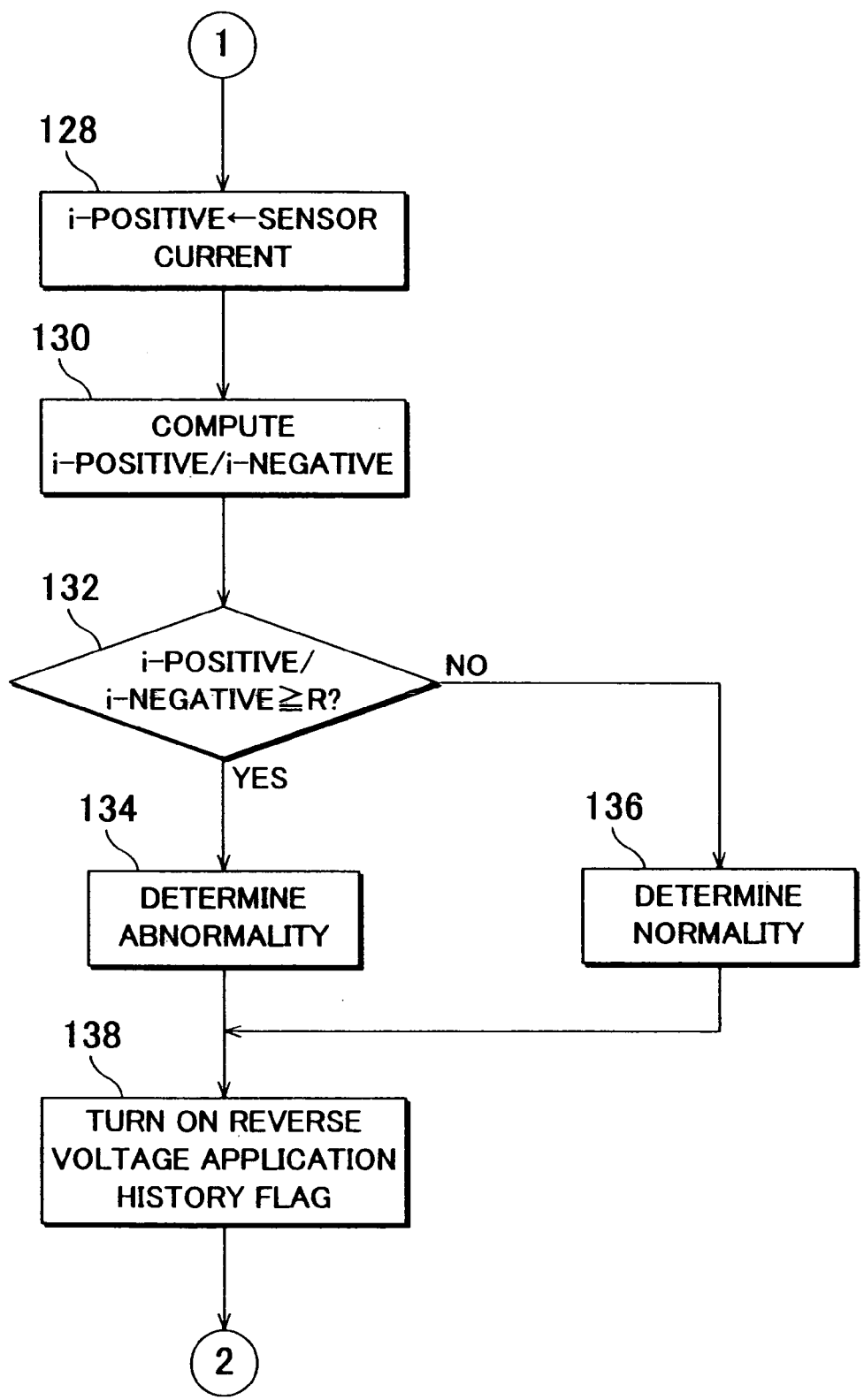

FIGS. 6A and 6B are flowcharts of the routine executed by the engine computer 30 in this embodiment. It is assumed that the routine shown in FIGS. 6A and 6B is activated on a predetermined cycle during operation of the internal combustion engine.

In the routine shown in FIGS. 6A and 6B, it is first distinguished whether or not a sufficient exhaust pressure is being generated. Specifically, it is distinguished whether or not the amount of intake air Ga is greater than a criterion value G (step 100). In the case where the exhaust pressure is small, exhaust gas will not enter the atmosphere layer 18 even if there is a crack in the air-fuel ratio sensor 10. The criterion value G is a value for determining whether the exhaust pressure is high enough to cause exhaust gas to enter the atmosphere layer 18.

If the condition Ga>G is not satisfied, it is determined that exhaust gas will not enter the atmosphere layer 18 even if there is a crack. The system of this embodiment is not able to detect a crack under such conditions. In this case, a reverse voltage application history flag is turned off (step 102). Next, a forward voltage is applied to the air-fuel ratio sensor 10 (step 104). Subsequently, in order to indicate that the applied voltage is the forward voltage, a forward voltage application flag is turned on (step 106), and then the forward voltage application flag is turned off (step 108).

If at step 100, the condition Ga>G is satisfied, it is determined that an environment for the entry of exhaust gas into the atmosphere layer 18 is substantially complete. In this case, it is then determined whether the reverse voltage application history flag is off (step 110).

The reverse voltage application history flag is turned on when the failure determination ends, as described below. Therefore, if Ga>G is satisfied, the failure determination has ended, the condition at step 110 is not satisfied. In this case, there is no need to further continue the process for failure determination, and the present process cycle is promptly ended.

On the other hand, before the failure determination is ended, it is determined that the reverse voltage application history flag is off at step 110. In this case, it is subsequently distinguished whether the reverse voltage application flag was on during the previous process cycle and the forward voltage application flag is on during the present process cycle (step 112).

When step 112 is executed for the first time after it is recognized that Ga>G is satisfied, the forward voltage application flag is on and the reverse voltage application flag is off. Therefore, at this time point, the condition of step 112 is not satisfied. In this case, it is subsequently distinguished whether or not the reverse voltage application time has reached a set time T (step 114).

The aforementioned "backward voltage application time" is an elapsed time after the voltage applied to the air-fuel ratio sensor 10 is changed to the voltage. When the process of step 114 is first executed after Ga>G is satisfied, the application of the reverse voltage has not begun, and therefore it is determined at step 114 that the condition is not satisfied. In this case, a process for applying the reverse voltage is subsequently executed (step 116). Next, the reverse voltage application flag is turned on (step 118), and the forward voltage application flag is turned off (step 120), and then the present process cycle ends.

If the next cycle is activated while the condition of Ga>G is still satisfied, it is determined at step 112 that although the reverse voltage application flag in the previous cycle was on, the forward voltage application flag in the present cycle is not on. That is, it is determined at step 112 that the condition is not satisfied. After that, the determination that the condition is not satisfied is repeatedly made at step 112 until the forward voltage application flag is tuned on.

If the reverse voltage application time reaches the set time T while the determination that the condition is not satisfied is made at step 112 repeatedly, it is then determined at step 114 that the condition is satisfied. In this case, subsequently the absolute value of the sensor current (reverse current) that is present at that time point is stored as "i-negative" (step 122). That is, the reverse current occurring at the time point when the reverse voltage application time reaches T is measured as "i-negative".

After the measurement of i-negative ends, the voltage applied to the air-fuel ratio sensor 10 is changed to the forward voltage (step 124). Subsequently, after the forward voltage application flag is turned on (step 126), the present process cycle is ended.

If the next process cycle is activated while Ga>G continues to be met, it is determined at step 112 that the reverse voltage application flag of the previous cycle is on and the forward voltage application flag of the present cycle is on. In this case, after step 112, the sensor current immediately following the changing of the application voltage to the forward voltage, is measured at "i-positive" (step 128).

Next, the electric current ratio (i-positive/i-negative) is computed (step 130). Then it is distinguished whether or not the current ratio (i-positive/i-negative) is greater than or equal to a criterion value R (step 132). If there is a sensor crack present, the i-negative would be smaller than the i-positive, and therefore the electric current ratio (i-positive/i-negative) increases. Therefore, if it is recognized that (i-positive/i-negative)≧R is satisfied, determination of abnormality is made to indicate the occurrence of a sensor crack (step 134). On the other hand, if it is judged that (i-positive/i-negative)≧R is not satisfied, it can be judged that a sensor crack has not occurred. In this case, determination of normality is made (step 136).

After the above-described process ends, the reverse voltage application history flag is turned on (step 138). Then, the condition of step 110 is not satisfied, so that the process for failure detection (steps 112 to 138) is skipped. Then, if Ga>G temporarily is not satisfied, the reverse voltage application flag is turned off (see step 102), and the process prepared for the execution of the failure detection.

As described above, the system according to this embodiment computes an electric current ratio (i-positive/i-negative) that does not contain the influence of the impedance by correcting the i-negative where both the influence of the oxygen concentration in the atmosphere layer 18 and the influence of the impedance are superposed, through the use of the i-positive where mainly the influence of the impedance alone is superposed. Then, the system is able to accurately determine the presence/absence of a sensor crack without being affected by fluctuations in the impedance, by comparing the electric current ratio (i-positive/i-negative) with the criterion value R.

Furthermore, in this embodiment, the set time T during which the reverse voltage is to be applied is set at about 100 to 200 msec. The output of the air-fuel ratio sensor 10 is used for the air-fuel ratio feedback control of the internal combustion engine. During application of the reverse voltage, the output thereof cannot be used for the feedback control. Therefore, it is desirable that the application time of the reverse voltage (set time T) be sufficiently short. On the other hand, if the set time T is excessively short, remarkable decrease does not occur in the i-negative even if exhaust gas enters the atmosphere layer 18. The time of 100 to 200 msec for the set time T is sufficient time for a detectable reduction in the i-negative to occur. A set time T of 100 to 200 msec also does not unreasonably interfere with the execution of the feedback control. Therefore, according to the system of this embodiment, it is possible to realize the high-accuracy detection of a sensor crack without deterioration of the control accuracy of the air-fuel ratio.

Incidentally, in the above-described first embodiment, the value obtained by correcting the i-negative by the i-positive that has a strong correlation with the impedance is compared with the criterion value R to determine the presence/absence of a sensor crack. However, the determination process is not limited to the above-described process. That is, a corrected criterion value (e.g., R*i-positive) may be determined by correcting the criterion value R by the i-positive, and the presence/absence of a sensor crack may be determined by comparing the corrected criterion value with the i-negative.

Furthermore, although in the first embodiment, the object of the failure detection is the air-fuel ratio sensor 10, the invention is not limited thereto. That is, the object of the failure detection may also be an oxygen sensor that selectively produces a rich output or a lean output. This also applies to the other embodiments described below.

In the first embodiment, the air-fuel ratio sensor 10 may be regarded as an "exhaust gas sensor" in the invention, and the i-positive and the electric current ratio (i-positive/i-negative) may be regarded as an "impedance correlation value" and a "corrected value", respectively, in the invention. Furthermore, the engine computer 30 can implement the functions of the "reverse voltage application device" and the "reverse electric current detection device". Still further, the engine computer 30 can implement the function of an "impedance correlation value acquisition device" by executing the process of step 128, and an "amendment device" by executing the process of step 132, and a "failure detection portion" by executing the process of step 132.

Furthermore, in the first embodiment, by having the engine computer 30 compute the corrected criterion value (R*i-positive) on the basis of the i-positive, it is possible to implement the functions of a "corrected criterion value computation device" in the invention. Similarly, by having the engine computer 30 to determine where there is a crack in the sensor based on the comparison of i-negative with the corrected criterion value, it is possible to implement the functions of a "failure detection portion" in the invention.

Still further, in the first embodiment, the set time T during which the reverse voltage is to be applied may be regarded as a "stabilization time" in the invention. Furthermore, herein, a function of a "forward voltage application device" can be implemented through the engine computer 30.

Next, with reference to FIGS. 7 and 8, a second embodiment of the invention will be described. The system of this embodiment can be realized by using a hardware construction similar to that in the first embodiment and causing the engine computer 30 to execute a routine shown in FIGS. 8A and 8B, which will be described below.

Figures 7A, 7B:
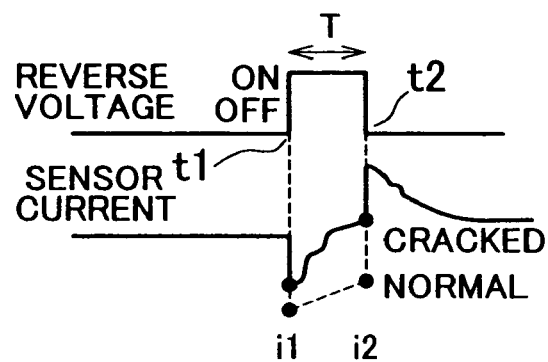
FIGS. 7A and 7B are timing charts for describing a technique used to determine the presence/absence of a sensor crack in a second embodiment.

FIGS. 7A and 7B are timing charts for describing a technique used in this embodiment to determine whether there is a sensor crack. More specifically, FIG. 7a is a diagram showing a pattern of the voltage application to the air-fuel ratio sensor 10.

FIG. 7B is a diagram in which the sensor current during normality and the sensor current when a sensor crack has occurred are represented in comparison.

FIGS. 7A and 7B are similar to FIGS. 4A and 4B, respectively, which show operations of the first embodiment. That is, FIG. 7A shows that a reverse voltage is applied during the period of time from time t1 to time t2, and outside of that period, the applied voltage is set as a forward voltage. In this case, the sensor current (negative current) that occurs immediately following the beginning of the application of the reverse voltage (time t1), and the sensor current (positive current) that occurs immediately following the change to the forward voltage (time t2) assume values that are in accordance with the impedance of the air-fuel ratio sensor 10 regardless of the presence/absence of a sensor crack as described above. The sensor current (negative current) occurring immediately before the change to the forward voltage (time t2) is a value determined by the oxygen concentration in the atmosphere layer 18 (i.e., the presence/absence of a sensor crack) and by the impedance.

In the first embodiment, the sensor current (i-negative in FIG. 4B) immediately before the change to the forward voltage is corrected by the sensor current (i-positive in FIG. 4B) that occurs immediately after the change to the forward voltage, so as to determine a current ratio (i-positive/i-negative), which is then used as the basis for determining whether there is a sensor crack. The sensor current that occurs immediately after the reverse voltage is applied is also a value that corresponds to the impedance, as in the case of the sensor current that occurs immediately after the change to the forward voltage. Therefore, the determination similar to that in the first embodiment can also be realized by correcting the sensor current (i2 in FIG. 7B) generated immediately before the change to the forward voltage by the sensor current (i1 in FIG. 7B) generated immediately after the reverse voltage is applied. Therefore, the system of this embodiment uses that technique to determine the presence/absence of a sensor crack.

Figure 8A:
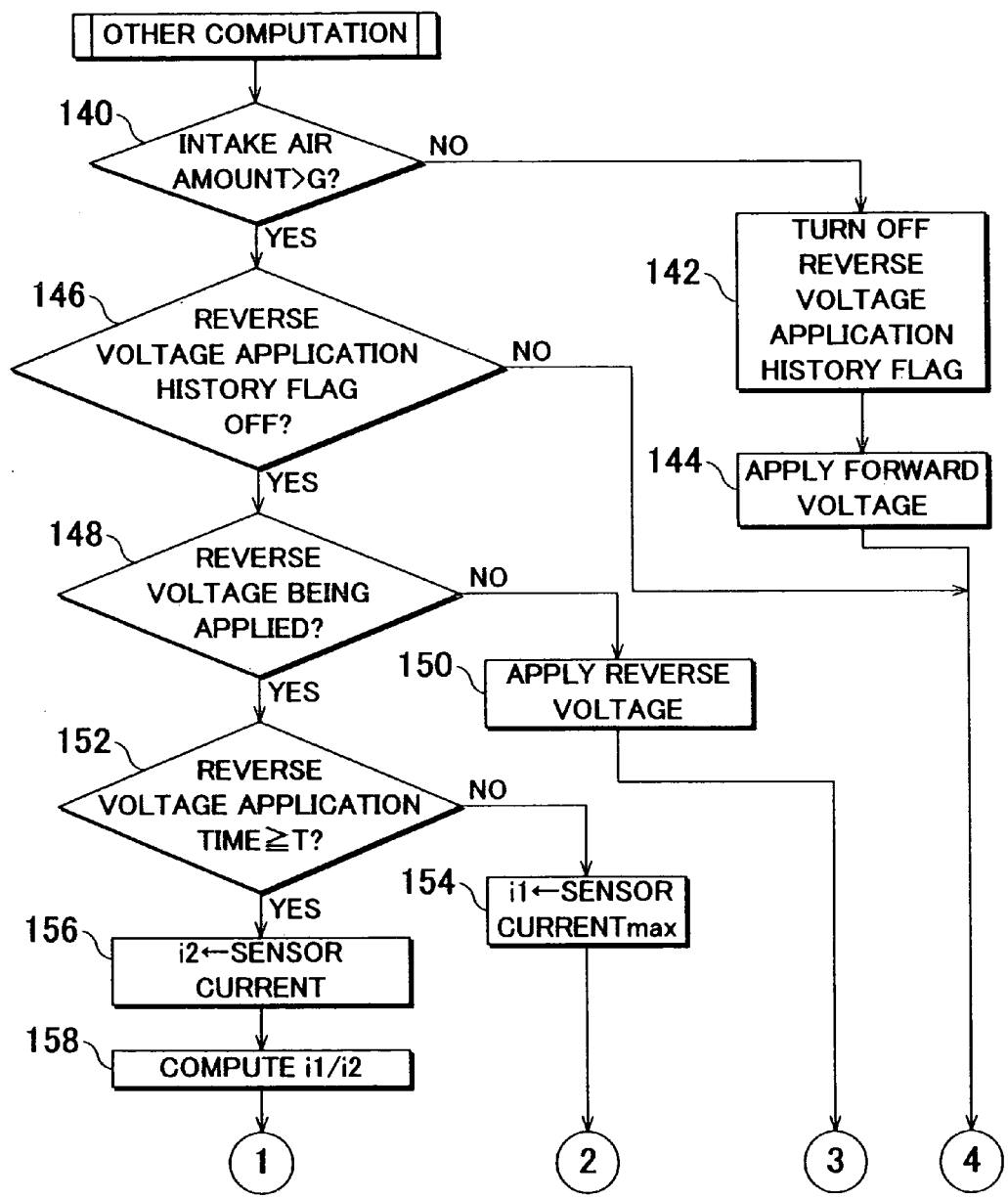
FIGS. 8A and 8B are flowcharts of a routine executed in the second embodiment.
Figure 8B:
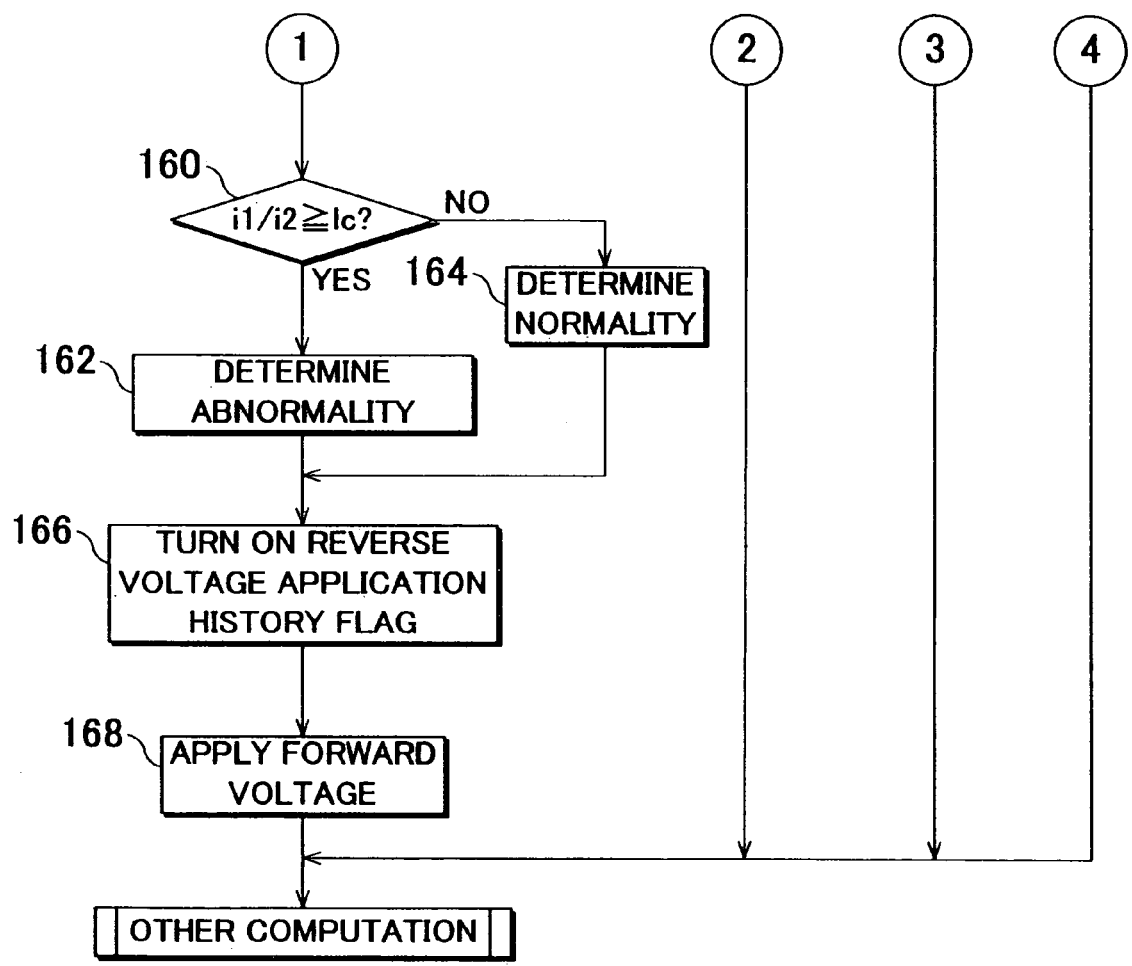

FIGS. 8A and 8B are flowcharts of the routine executed by the engine computer 30 in this embodiment. It is assumed that the routine shown in FIGS. 8A and 8B is activated on a predetermined cycle during operation of the internal combustion engine.

In the routine shown in FIGS. 8A and 8B, it is first distinguished whether or not the amount of intake air Ga is greater than a criterion value G (step 140). If Ga>G is not satisfied, it is determined that the exhaust pressure is insufficient to allow the detection of a sensor crack. In this case, the reverse voltage application history flag is turned off (step 142), and the forward voltage is applied (step 144). After that, the present process cycle ends.

On the other hand, if it is recognized that Ga>G is satisfied, it is determined that the exhaust pressure is sufficient to allow the detection of a sensor crack. In this case, it is then determined whether the reverse voltage application history flag is off (step 146).

When step 146 is executed for the first time after the condition Ga>G has been satisfied, the reverse voltage application history flag is off. Therefore, at this time point, the condition of step 146 is satisfied. In this case, it is then distinguished whether or not the reverse voltage is being applied (step 148).

At the stage where step 148 is executed for the first time after the condition Ga>G is satisfied, the application of the reverse voltage is not begun yet. In this case, it is determined that the condition of step 148 is not satisfied, and then the reverse voltage is applied (step 150). After that, the present process cycle ends.

If the next cycle is activated while the condition of Ga>G is still satisfied, it is now determined at step 148 that the reverse voltage is being applied. In this case, it is then distinguished whether or not the reverse voltage has been applied for set time period T (step 152).

The aforementioned "reverse voltage application time" is an elapsed time following the switching of the voltage applied to the air-fuel ratio sensor 10 to the reverse voltage. When the process of step 152 is executed for the first time after Ga>G is satisfied, the reverse voltage duration has not reached the set time T. Therefore, at this state, it is determined that the condition of step 152 is not satisfied. In this case, a process of measuring a maximum absolute value of the sensor current (negative current) as a first reverse current i1 is then executed (step 154).

The process of step 154 is executed repeatedly in every one of the next and subsequent process cycles of the routine shown in FIGS. 8A and 8B until the reverse voltage duration reaches T, provided that the relationship of Ga>G is satisfied. At step 154, specifically, if the absolute value of the latest sensor current is greater than the presently stored value i1, i1 is updated to its latest value. According to this process, the greatest value of the sensor current occurring before the reverse voltage duration reaches the set time T can be stored as a first reverse current i1.

After the applied voltage is switched from the forward voltage to the reverse voltage, the sensor current increases to the maximum value in accordance with an appropriate time constant. This maximum value is a value that corresponds to the impedance of the air-fuel ratio sensor 10 regardless of the presence/absence of a sensor crack. Therefore, according to the above-described process, the sensor current that corresponds to the impedance of the air-fuel ratio sensor 10 can be appropriately stored as reverse current i1.

If the reverse voltage duration reaches the set time T while the relationship of Ga>G is satisfied, it is determined at step 152 that the condition is satisfied. In this case, the sensor current occurring at that time point is measured as a second reverse current i2 (step 156). The set time T is set as a time (about 100 to 200 msec) that does not adversely affect the air-fuel ratio feedback control and that can bring the reverse current close, to some degree, to a convergence value.

In the case where there is a sensor crack, the oxygen concentration in the atmosphere layer 18 is low, and therefore the sensor current greatly decreases during the set time T. On the other hand, if there is no sensor crack, oxygen is sufficiently present in the atmosphere layer 18, and therefore such a great decrease of the sensor current does not occur during the set time T. Therefore, according to the process of step 156, the sensor current where the information regarding the presence/absence of a sensor crack is superposed can be properly stored as a second reverse current i2.

In the routine shown in FIGS. 8A and 8B, a value (electric current ratio (i1/i2) in which the reverse current containing the information regarding the presence/absence of a sensor crack, that is, the second reverse current i2, is corrected by the reverse current containing the information regarding the impedance, that is, the first reverse current i1, is computed (step 158).

Subsequently, it is distinguished whether or not the electric current ratio (i1/i2) is greater than or equal to a criterion value Ic (step 160). If there is a sensor crack, the value i2 decreases relative to the value i1, and therefore the value "i1/i2" increases. Therefore, if it is recognized that (i1/i2)≧Ic is satisfied, it is determined that there is a crack in the sensor (step 162). On the other hand, if it is recognized that (i1/i2)≧Ic is not satisfied, it is judged that there is no sensor crack, and thus normality is determined (step 164).

After the above-described process ends, the reverse voltage application history flag is turned on (step 166) to indicate that the failure determination process has ended. Then, the process of switching the applied voltage to the forward voltage is performed (step 168), and the present process cycle ends.

If the routine is activated while Ga>G is maintained, it is determined at step 146 that the reverse voltage application history flag is not off. As a result, the process cycle is promptly ended, so as to avoid unnecessary repetitions of the failure detection process.

As described above, according to the system of this embodiment, the electric current ratio (i1/i2) that does not contain the influence of the impedance can be computed by correcting the value i2 where the influence of the oxygen concentration in the atmosphere layer 18 and the influence of the impedance are both superposed, with the value i1 where mainly the influence of the impedance alone is superposed. Then, by comparing the electric current ratio (i1/i2) with the criterion value Ic, the system is able to accurately determine the presence/absence of a sensor crack without being affected by fluctuations of the impedance, as in the case of the first embodiment.

Incidentally, in the above-described second embodiment, the presence/absence of a sensor crack is determined by comparing a value obtained through correction of the second reverse current i2 by the first reverse voltage i1 that has a strong correlation with the impedance, with the criterion value Ic. However, the technique of the determination is not limited to that technique. For example, a corrected criterion value (e.g., Ic*i1) may be obtained by correcting the criterion value Ic by the value i1, and the obtained value and the value i2 may be compared to determine the presence/absence of a sensor crack.

Furthermore, in the second embodiment, the presence/absence of a sensor crack is determined during ordinary operation of the engine. However, the determination may also be performed in a situation where the fuel-cut is being executed in an internal combustion engine. Hereinafter, a technique of determining the presence/absence of a sensor crack during the fuel-cut will be described with reference to FIGS. 9A to 9D.

FIG. 9A shows a waveform representing the timing of executing the fuel-cut. FIG. 9B is a diagram representing a pattern of the voltage applied to the air-fuel ratio sensor 10. FIG. 9C is a diagram showing the oxygen concentrations in the atmosphere layer 18 during normality (broken line) and when a crack has occurred (solid line) are represented in contract. FIG. 9D shows a waveform of the sensor current.

FIGS. 9A to 9D show an example where the fuel-cut is executed over the period of a time t1 to a time t3, and the reverse voltage is applied to the air-fuel ratio sensor 10 from the time t1 to a time t2. In the case where there is no crack in the air-fuel ratio sensor 10, the atmosphere layer 18 is always filled with the atmosphere. Therefore, in this case, that is, in the case of "normality" in FIG. 9C, the oxygen concentration in the atmosphere layer 18 is always stable at a sufficiently high value as indicated by a broken line in FIG. 9C.

In contrast, in the case where there is a sensor crack, gas that flows through the exhaust passage enters the atmosphere layer 18, and lowers the oxygen concentration in the atmosphere layer 18. During ordinary operation of the internal combustion engine, exhaust gas having an air-fuel ratio near the stoichiometric air-fuel ratio passes in the exhaust passage. On the other hand, during the fuel-cut, air containing no fuel component passes in the exhaust passage. Therefore, if there is a sensor crack, the oxygen concentration in the atmosphere layer 18 stably remains at a low value until the fuel-cut begins, as indicated by a solid line in FIG. 9C. After the fuel-cut begins, the oxygen concentration tends increase. Then, after the fuel-cut ends, the oxygen concentration starts to drop again.

In the case where the air-fuel ratio sensor 10 is normal and oxygen is sufficiently present in the atmosphere layer 18, the absolute value of the second reverse current i2 is slightly smaller than the absolute value of the first reverse current i1 as indicated by a broken line in FIG. 9D. On the other hand, in the case where there is a sensor crack, the absolute value of the second reverse current i2 is larger than the absolute value of the first reverse current i1 as indicated by a solid line in FIG. 9D since the oxygen concentration in the atmosphere layer 18 rises during the fuel-cut.

Therefore, in the case where the reverse voltage is applied concurrently with the fuel-cut, the electric current ratio (i1/i2) assumes a large value during normality, and assumes a small value when there is a sensor crack. Therefore, in this case, it is necessary that the basis for determination be reversed from that in the second embodiment (see step 160), that is, normality determination be made if (i1/i2)>Ic' is satisfied, and abnormality determination is made if it is not satisfied (Ic' is a criterion value suitable for the modification).

That is, although in the foregoing second embodiment, occurrence of a sensor crack is determined if (i1/i2)>Ic is satisfied, the invention is not limited so. That is, it is also permissible that the presence/absence of a sensor crack be determined during execution of the fuel-cut and that the occurrence of a sensor crack be recognized when (i1/i2)>Ic' is not satisfied.

Incidentally, in the second embodiment, the first reverse current i1 can be regarded as an "impedance correlation value" in the invention, and the electric current ratio (i1/i2) can be regarded as a "corrected value" in the invention. Furthermore, the engine computer 30 can realize an "impedance correlation value acquisition device" in the invention by executing the process of step 154, and a "corrected value computation device" in the invention by executing the process of step 158, and a "failure detection device" in the invention by executing the process of step 160.

Furthermore, in the second embodiment, by causing the engine computer 30 to compute the corrected criterion value (Ic*i1) on the basis of the value i1, it is possible to realize a "corrected criterion value computation device" in the invention. Similarly, by causing the engine computer 30 to determine the presence/absence of a sensor crack on the basis of the comparison of the value i2 with the corrected criterion value, it is possible to realize a "failure detection portion" in the invention.

Next, a third embodiment of the invention will be described with reference to FIGS. 10A, 10B and 11. The system of this embodiment can be realized by using the hardware construction of the first embodiment and causing the engine computer 30 to execute a routine shown in FIGS. 11A and 11B, which will be described below.

As in the case of the second embodiment, the system of this embodiment obtains an electric current ratio (i1/i2) on the condition that the amount of intake air Ga exceeds the criterion value G, and determines the presence/absence of a sensor crack on the basis of the electric current ratio (i1/i2). FIGS. 10A and 10B are diagrams for describing the influences that the size of the criterion value G has on the electric current ratio (i1/i2).

Specifically, FIG. 10A is a diagram for describing the phenomenon that occurs when the criterion value G is set at a small value. In the case where the criterion value G is set at a small value, the condition of Ga>G is satisfied under a situation where the exhaust pressure is relatively small. However, under such a situation, occurrence of a large crack allows exhaust gas to enter the atmosphere layer 18 whereas if the crack is small, exhaust gas will not enter the atmosphere layer 18 even if Ga>G satisfied for a long time.

The electric current ratio (i1/i2) is larger if the amount of exhaust gas entering the atmosphere layer 18 is larger. Therefore, the electric current ratio (i1/i2) of a sensor with a small sensor crack assumes substantially the same value as the electric current ratio (i1/i2) of a normal sensor, regardless of the time of continuation of Ga>G as shown in FIG. 10A. Therefore, in the case where the criterion value G is set at a small value, an event occurs where occurrence of a small sensor crack cannot be detected.

FIG. 10B is a diagram for describing a phenomenon that occurs in the case where the criterion value G is set at a large value. In this case, sufficiently great exhaust pressure is generated under a situation where Ga>G is satisfied. Therefore, as the situation continues, exhaust gas gradually enters the atmosphere layer 18. Therefore, if Ga>G continues to be satisfied for a sufficiently long time, the electric current ratio (i1/i2) of the sensor with a small sensor crack assumes a value that is distinct from the electric current ratio (i1/i2) of the normal sensor as show in FIG. 10B. Therefore, in this embodiment, in order to detect, with good accuracy, the occurrence of a small sensor crack as well, the criterion value G is set at a sufficiently large value, and execution of the abnormality determination based on the electric current ratio (i1/i2) is permitted provided that Ga>G continues to be satisfied for a sufficiently long time.

Figure 11A:
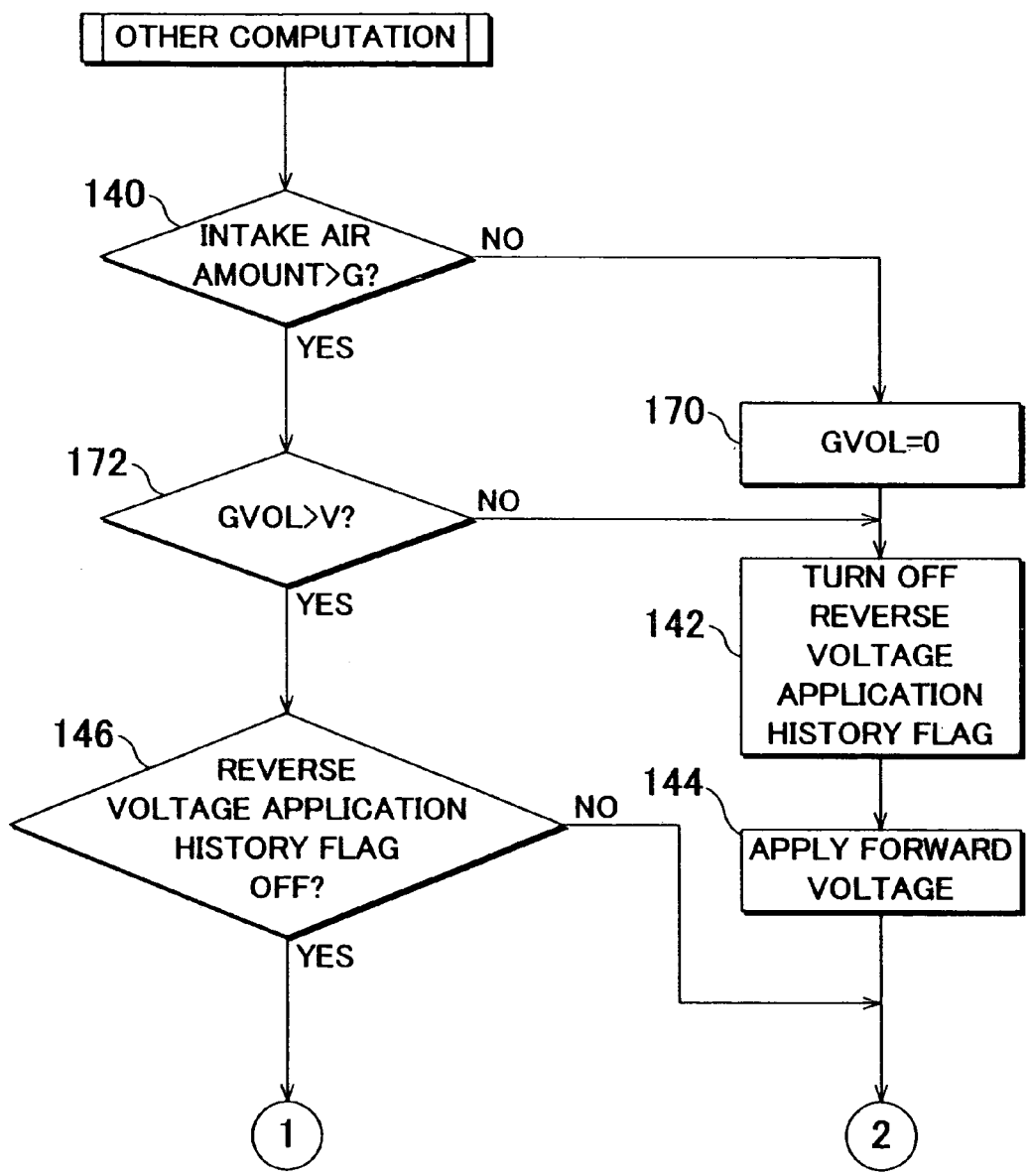
FIGS. 11A and 11B are flowcharts of a routine executed in a third embodiment of the invention.
Figure 11B:
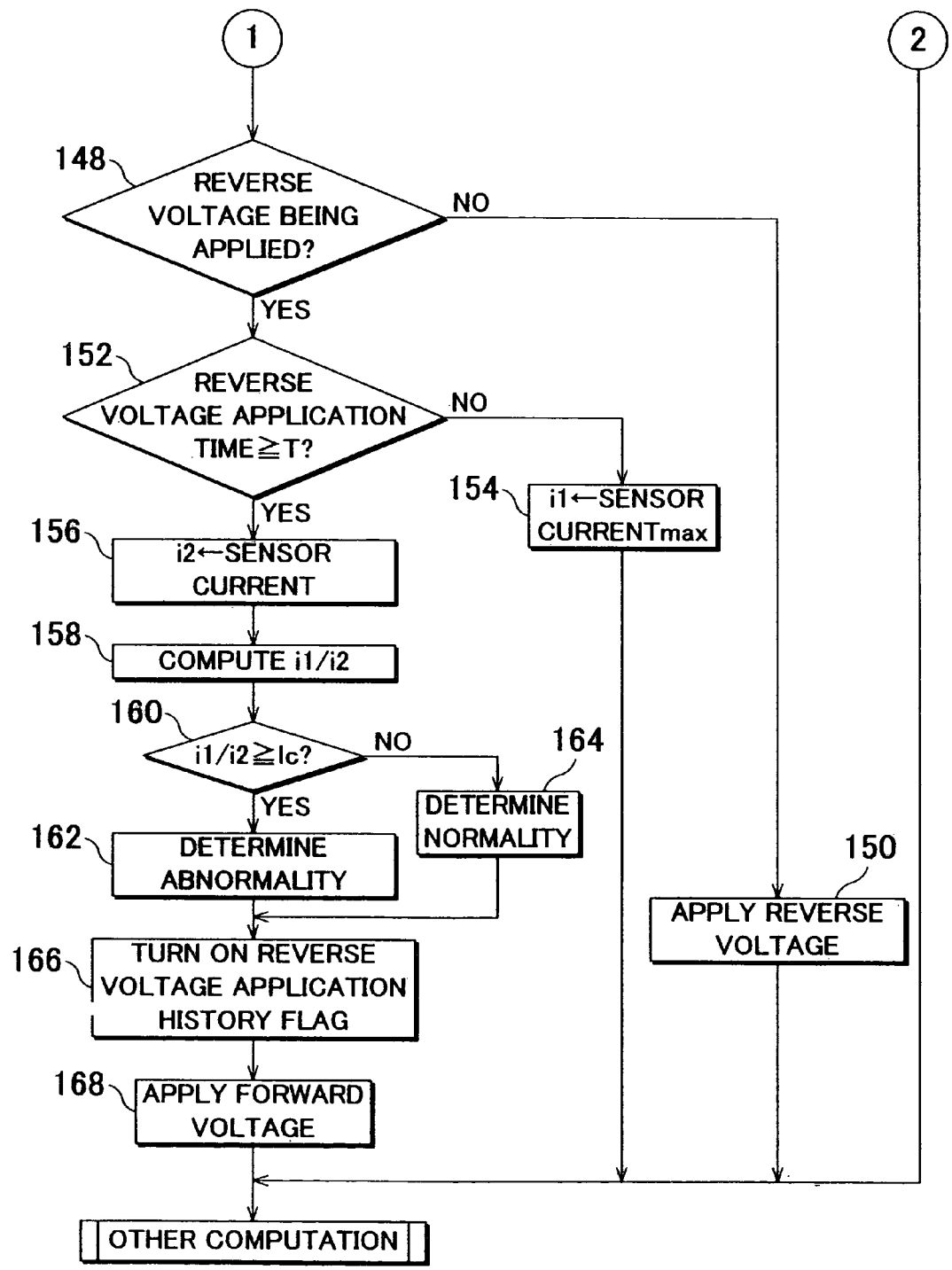

FIGS. 11A and 11B are flowcharts of a routine executed by the engine computer 30 in this embodiment. The routine shown in FIGS. 11A and 11B is substantially the same as the routine shown in FIGS. 8A and 8B, except that steps 170 and 172 are inserted. However, in the routine shown in FIGS. 11A and 11B, it is assumed that the criterion value G used at step 140 is an amount of intake air that is sufficient to cause exhaust gas to enter the atmosphere layer 18 even in the case where only a small sensor crack is formed in the air-fuel ratio sensor 10.

In the routine shown in FIGS. 11A and 11B, if it is determined at step 140 that Ga>G is not satisfied, the integrated amount of air GVOL is cleared to zero (step 170). After that, the process of steps 142 and 144 is executed. The integrated amount of air GVOL is a value obtained by integrating the amount of intake air Ga during every cycle. Due to execution of the process of step 170, the integrated amount of air GVOL substantially becomes an integrated value of the amount of intake air Ga provided during the period when Ga>G is continuously satisfied.

If Ga>G is satisfied at step 140, it is then distinguished whether or not the integrated amount of air GVOL exceeds a criterion amount V (step 172). In the case of a small sensor crack, a certain amount of time following the holding of Ga>G is needed before a significant amount of exhaust gas enters the atmosphere layer 18. The criterion amount V is a value that ensures sufficient time has elapsed for exhaust gas to enter the atmosphere layer. Therefore, if it is distinguished that GVOL>V is not satisfied, it can be determined that there is a possibility that a sufficient amount of exhaust gas may not have entered the atmosphere layer 18 through the small crack.

If a sufficient amount of exhaust gas does not enter the atmosphere layer 18, a sensor crack cannot be detected. Therefore, if at step 172 it is determined that GVOL>V is not satisfied, the present process cycle is promptly ended without execution of a sensor crack detecting process. According to the process described above, it is possible to reliably avoid missing a small sensor crack.

On the other hand, in the case where at step 172 the holding of GVOL>V is recognized, it can be assured that a sufficient amount of exhaust gas has entered the atmosphere layer 18 if a sensor crack has occurred, regardless of the size of the sensor crack. In this case, the process of step 146 and subsequent steps is executed to determine the presence/absence of a sensor crack.

As described above, according to the routine shown in FIGS. 11A and 11B, if a sensor crack is present, the determination regarding the presence/absence of a sensor crack can be permitted only under the condition where the occurrence of the sensor crack can be reliably detected even if the crack is small. Therefore, according to this system, the presence/absence of a sensor crack can be accurately determined without being affected by the magnitude of a sensor crack.

In the above-described third embodiment, the integrated amount of air GVOL exceeding the criterion amount V is set as a condition in order to ensure that a sufficient amount of exhaust gas has entered the atmosphere layer 18 even in the case of a small sensor crack. However, the technique for such assurance is not limited to this technique. That is, it can be ensured that a sufficient amount of exhaust gas has entered, by seeing whether or not the relationship of Ga>G has continued for a predetermined time.

Furthermore, the entry of sufficient amount of exhaust gas may also be ensured on the basis of the exhaust pressure, not the amount of intake air Ga. That is, if an environment where the exhaust pressure is greater than or equal to a predetermined value continues for a predetermined time, the determination regarding the presence/absence of a sensor crack may be permitted.

Furthermore, the above-described third embodiment is a combination of the determination regarding the condition of GVOL>V with the second embodiment. However, this combination does not limit the invention. That is, the determination regarding the condition of GVOL>V may also be combined with the first embodiment.

Incidentally, in the third embodiment, the engine computer 30 realizes an "exhaust pressure determination device" in the invention by executing the process of step 140, and an "execution condition determination device" in the invention by executing the process of step 172.

Next, a fourth embodiment of the invention will be described with reference to FIGS. 12A and 12B. The system of this embodiment can be realized in the hardware construction of the first embodiment by causing the engine computer 30 to execute a routine shown in FIGS. 12A and 12B which will be described below.

In the systems of the foregoing first to third embodiments, detection of a sensor crack is permitted if the amount of intake air Ga exceeds the criterion value G Under an environment where Ga>G is satisfied, exhaust gas enters the atmosphere layer 18 provided that there is a sensor crack. In this case, the electric current ratio (i-positive/i-negative) (see FIGS. 4A and 4B) or the electric current ratio (i1/i2) (see FIGS. 7A and 7B) becomes a great value, so that the detection of a sensor crack becomes possible.

Incidentally, during operation of the internal combustion engine, a fuel-cut is performed, for example, if the throttle valve is closed under an environment where the engine rotation speed NE is sufficiently high. During execution of the fuel-cut, air flows into the exhaust passage. If air passes around the air-fuel ratio sensor 10 with a sensor crack, the atmosphere layer 18 is scavenged, so that the exhaust gas concentration therein drops. Then, if the exhaust gas concentration in the atmosphere layer 18 drops, the electric current ratio (i-positive/i-negative), (i1/i2) approaches a normal value, so that the detection of a sensor crack becomes difficult.

The aforementioned fuel-cut is executed when the throttle valve is closed, that is, when the amount of intake air Ga is reduced. Therefore, in the systems of the first and third embodiments, the determination as to whether a crack is present in a sensor is not performed during execution of the fuel-cut. Hence, according to these systems, it does not happen that a false determination is made regarding the presence/absence of a sensor crack in association with the execution of the fuel-cut during deceleration.

However, in the internal combustion engine, the fuel-cut for preventing overspeed rotation is executed in some cases. That is, in the internal combustion engine, if the engine rotation speed NE reaches a permissible upper limit value, the fuel-cut is performed in order to avoid any further increase of the engine speed. This fuel-cut is performed when the amount of intake air Ga is sufficiently large. Therefore, in the systems of the first to third embodiments, an event can happen in which determination regarding the presence/absence of a sensor crack is made during the execution of the fuel-cut for preventing overspeed of the engine. According to such determination, an event where a sensor crack is missed can occur because the exhaust gas in the atmosphere layer 18 is scavenged. Therefore, in the system of this embodiment, as a condition for detection of a sensor crack, the state of the fuel-cut is determined. Specifically, during the execution of the fuel-cut, the detection of a sensor crack is prohibited even if the amount of intake air Ga is satisfied.

Figure 12A:
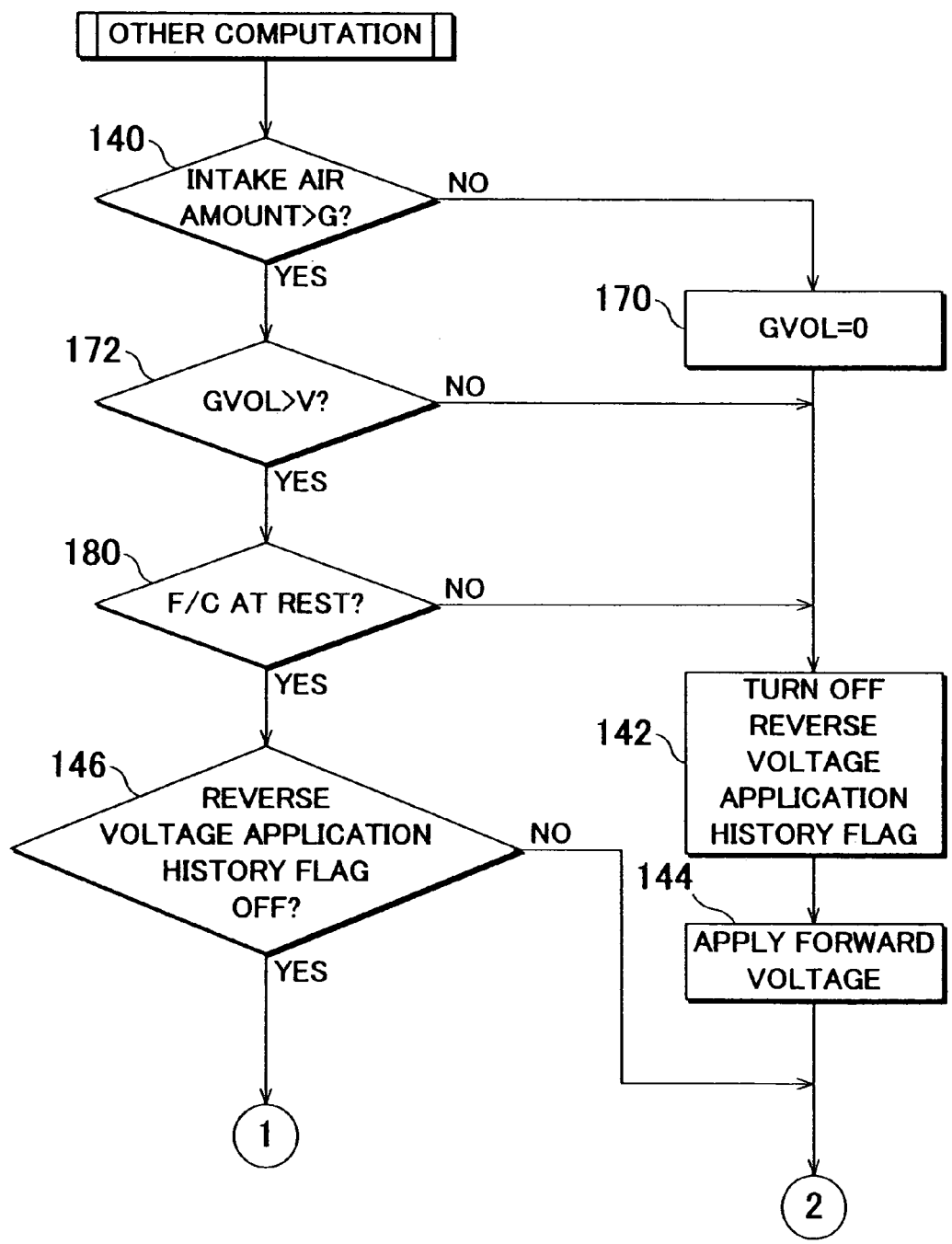
FIGS. 12A and 12B are flowcharts of a routine executed in a fourth embodiment of the invention.
Figure 12B:
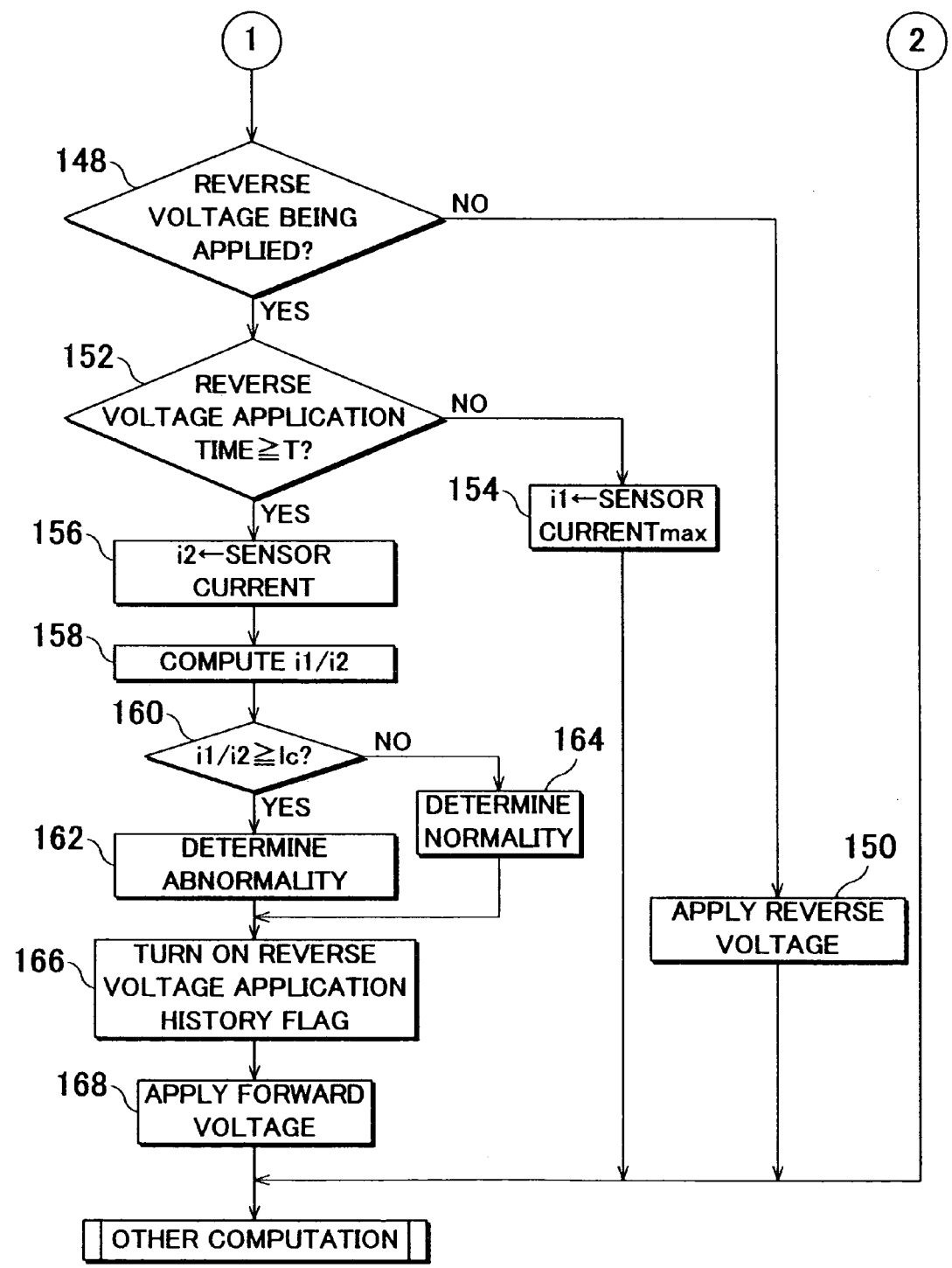

FIGS. 12A and 12B are flowcharts of a routine executed by the engine computer 30 in this embodiment. The routine shown in FIGS. 12A and 12B is substantially the same as the routine shown in FIGS. 11A and 11B, except that step 180 is inserted after step 172. That is, in the routine shown in FIGS. 12A and 12B, if it is determined at step 172 that the integrated amount of air GVOL exceeds the criterion amount V, it is then distinguished whether or not the fuel-cut is at rest (step 180).

As a result, if it is distinguished that the fuel-cut is at rest, the process of step 146 and subsequent steps is executed for the detection of a sensor crack. On the other hand, if execution of the fuel-cut is recognized at step 180, the detection of a sensor crack is prohibited, and then the process of steps 142 and 144 is executed. After that, the present process cycle ends.

According to the foregoing process, during execution of the fuel-cut, the detection of a sensor crack can be reliably prohibited. Therefore, the system of this embodiment is able to reliably prevent false determination regarding the presence/absence of a sensor crack from being made in association with the execution of the fuel-cut.

Incidentally, in the above-described fourth embodiment, the process of prohibiting the detection of a sensor crack during the fuel-cut is combined with the third embodiment. However, this does not limit the invention. That is, the process of prohibiting the detection of a sensor crack during the fuel-cut may also be combined with the first embodiment or the second embodiment.

Incidentally, in the above-described fourth embodiment, the engine computer 30 realizes a "fuel-cut device" in the invention by performing the fuel-cut during deceleration or engine overspeed, and an "execution prohibition device" in the invention by executing the process of step 180.

Next, a fifth embodiment of the invention will be described with reference to FIGS. 13A to 18. The system of this embodiment can be realized in the hardware construction of the first embodiment by causing the engine computer 30 to execute a routine shown in FIGS. 17A and 17B, which will be described below.

FIGS. 13A to 13C are timing charts for describing a technique used in this embodiment to determine the presence/absence of a sensor crack. More specifically, FIG. 13A shows a waveform representing the execution of the fuel-cut. FIG. 13B is a waveform representing changes in the voltage applied to the air-fuel ratio sensor 10. FIG. 13C is the waveform of the sensor current that flows through the air-fuel ratio sensor 10.

The apparatus of this embodiment applies a forward voltage to the air-fuel ratio sensor 10 before the fuel-cut begins (see FIG. 13B). During this period, the engine computer 30 is able to detect the exhaust air-fuel ratio on the basis of the sensor current.

When the fuel-cut begins, the applied voltage is changed at that time point to the reverse voltage (see FIG. 13B). At this time, the reverse current generated in association with the application of the reverse voltage is acquired as a first reverse current i1 (see FIG. 13C).

Before the fuel-cut begins, the air-fuel ratio in the exhaust passage is maintained near the stoichiometric air-fuel ratio. Therefore, if there is a sensor crack, exhaust gas will have already mixed in the atmosphere layer 18 when the fuel-cut is started. Particularly in the case where a large amount of exhaust gas has mixed in and the oxygen concentration in the atmosphere layer 18 has sufficiently dropped, the reverse current is small immediately after the application of the reverse voltage. The first reverse current i1 indicated by a solid line in FIG. 13C is a reverse current that occurs under such an environment.

When there is no crack leading to the atmosphere layer 18, the interior of the atmosphere layer 18 is filled with the atmosphere when the fuel-cut is started. In this case, the oxygen concentration in the atmosphere layer 18 is sufficiently high, so that the first reverse current i1 becomes large in absolute value as indicated by a broken line in FIG. 13C.

When a predetermined reverse voltage time t (e.g., 50 to 100 msec) elapses following the beginning of the fuel-cut, the applied voltage is returned to the forward voltage. After that, when the elapsed time following the beginning of the fuel-cut reaches a reverse voltage application interval Tint (e.g., 1 sec), the reverse voltage is applied again for just the reverse voltage application time t. The engine computer 30 acquires the reverse current that occurs at this time point, as a second reverse current i2 (see FIG. 5C).

During execution of the fuel-cut, air that does not contain fuel passes around the air-fuel ratio sensor 10. Therefore, if there is a sensor crack, the scavenging of the atmosphere layer 18 progresses and the oxygen concentration therein rises during the reverse voltage application interval Tint. As a result, the second reverse current i2 becomes a value that substantially corresponds to the oxygen concentration in the atmosphere, regardless of the presence/absence of a sensor crack.

After that, the engine computer 30 determines whether or not the absolute value of the second reverse current i2 is significantly larger than the absolute value of the first reverse current i1. If it is determined that the two values are not significantly different, it is determined that the air-fuel ratio sensor 10 is normal. In contrast, if it is determined that the absolute value of the second reverse current i2 is sufficiently larger than the absolute value of the first reverse current i1, it is determined that there is a sensor crack in the air-fuel ratio sensor 10.

Incidentally, the above-described detection technique for a sensor crack is based on the assumption that if there is a sensor crack, a significant amount of exhaust gas will have been mixed in the atmosphere layer 18 when the fuel-cut is started. However, this assumption does not always hold.

FIGS. 14A to 14C are timing charts in the case where the aforementioned assumption holds. On the other hand, FIGS. 15A to 15C are timing charts in the case where the assumption does not hold. Of the drawings, FIG. 14A and FIG. 15A show the amount of intake air Ga. FIG. 14B and FIG. 15B show the integrated amount of air GVOL. FIG. 14C and FIG. 15C indicate the state of the fuel-cut.

In the example shown in FIGS. 14A to 14C, the amount of intake air Ga exceeds the criterion value G at a time t1, and the integrated amount of air GVOL exceeds the criterion amount V at a time t2. After that, the throttle valve is suddenly closed. At a time t3, Ga becomes less than G, so that GVOL is reset to zero. Then, after a short delay time Tf, that is, at a time t4, the fuel-cut is begun.

According to the example shown in FIGS. 14A to 14C, an environment for the entry of exhaust gas from the site of a sensor crack into the atmosphere layer 18 is substantially complete until the time t3. On the other hand, after the time t3, the exhaust pressure sharply drops, so that an environment for the scavenging of the atmosphere layer 18 is established. However, if the delay time Tf from the time t3 to the time t4 when the fuel-cut is begun is sufficiently short, a significant amount of exhaust gas remains in the atmosphere layer 18 at the time t4. Therefore, in the case shown in FIGS. 14A to 14C, if the application of the reverse voltage begins simultaneously with the start of the fuel-cut, the aforementioned assumption holds, so that it is possible to detect a sensor crack.

FIGS. 15A to 15C show an example where the throttle valve is gently closed after the time t2. In this example, the fuel-cut begins at the time point (time t4) of elapse of a long delay time Tf after the amount of intake air Ga becomes less than the criterion value G at the time t3. In the case as shown in FIGS. 15A to 15C, after the time t3, the environment for the scavenging of the atmosphere layer 18 holds for a long time and the scavenging of the atmosphere layer 18 sufficiently progresses until the fuel-cut is begun. In this case, the aforementioned assumption has failed to hold at the time point of the beginning of the fuel-cut, so that an event where a sensor crack cannot be appropriately detected can happen.

Therefore, in this embodiment, the detection of a sensor crack by the technique shown in FIGS. 13A to 13C is permitted only when the integrated amount of air GVOL exceeds the criterion value G prior to the fuel-cut, and where the fuel-cut begins after the elapse of a sufficiently short time after the amount of intake air Ga has become lower than the criterion value G FIGS. 16A to 16E are timing charts for describing an operation performed when the sensor crack detection is carried out in accordance with the aforementioned rule. Specifically, FIG. 16A shows changes in the amount of intake air Ga. FIG. 16B shows changes in the integrated amount of air GVOL. FIG. 16C shows the state of a gas substitution flag described below. FIG. 16D shows changes in the delay time Tf. FIG. 16E indicates the state of the fuel-cut.

FIGS. 16A to 16E show an example where the amount of intake air Ga changes as in the case shown in FIGS. 14A to 14C. In the case where there is a sensor crack, it can be determined that sufficient exhaust gas has entered the atmosphere layer 18 at the time point (time t2) when the integrated amount of air GVOL exceeds the criterion amount V The gas substitution flag is a flag that is turned on at that time point, as shown in FIG. 16C. Therefore, in the system of this embodiment, if the gas substitution flag is on, it can be recognized that there is a history of sufficient entry of exhaust gas into the atmosphere layer 18.

The delay time Tf is the time that has elapsed from when the exhaust pressure is reduced so that an environment for the scavenging of the atmosphere layer 18 becomes substantially complete until when the beginning of the fuel-cut. Therefore, as shown in FIG. 16D, the delay time Tf is incremented from the time t3 when the amount of intake air Ga becomes less than the criterion value G to the time t4 when the fuel-cut is begun.

In this embodiment, the engine computer 30 determines whether the gas substitution flag is on when the fuel-cut is started and the delay time Tf is less than or equal to a determination permission wait time (hereinafter, referred to simply as "determination time") Ts. The determination time T2 is the time during which a significant amount of exhaust gas resides in the atmosphere layer 18 under a situation where an environment for the scavenging is substantially complete. Therefore, in the case where the aforementioned two conditions both hold, it can be determined that a sufficient amount of exhaust gas has mixed in the atmosphere layer 18.

FIGS. 16A to 16E show an example where both conditions at satisfied at the time point of the beginning of the fuel-cut. The system of this embodiment permits the detection of a sensor crack, only in such a case. Therefore, according to the system of this embodiment, it is possible to effectively prevent a false determination from being made under an environment where exhaust gas is not sufficiently present in the atmosphere layer 18.

Figure 17A:
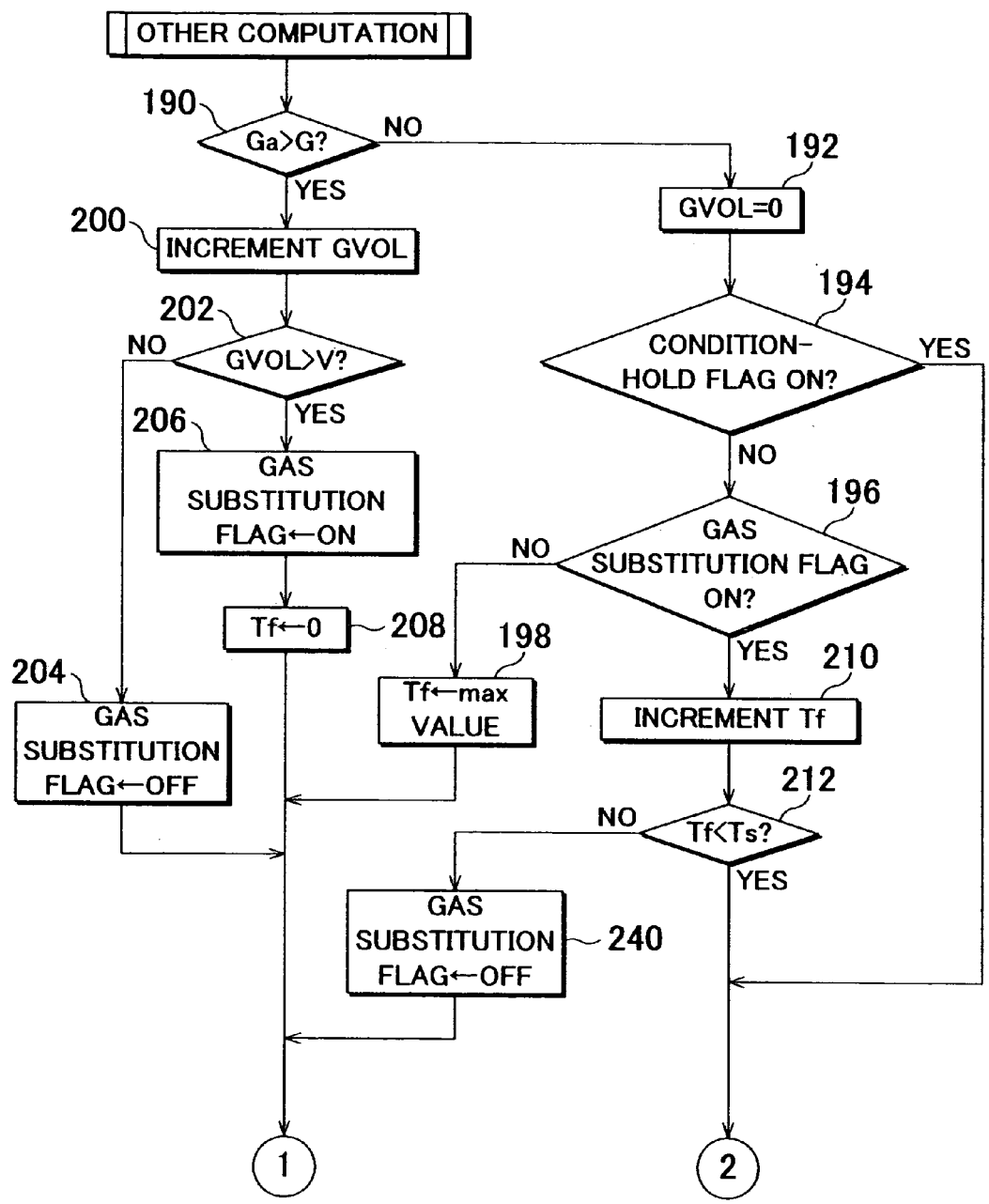
FIGS. 17A and 17B are flowcharts of a routine executed in the fifth embodiment.
Figure 17B:
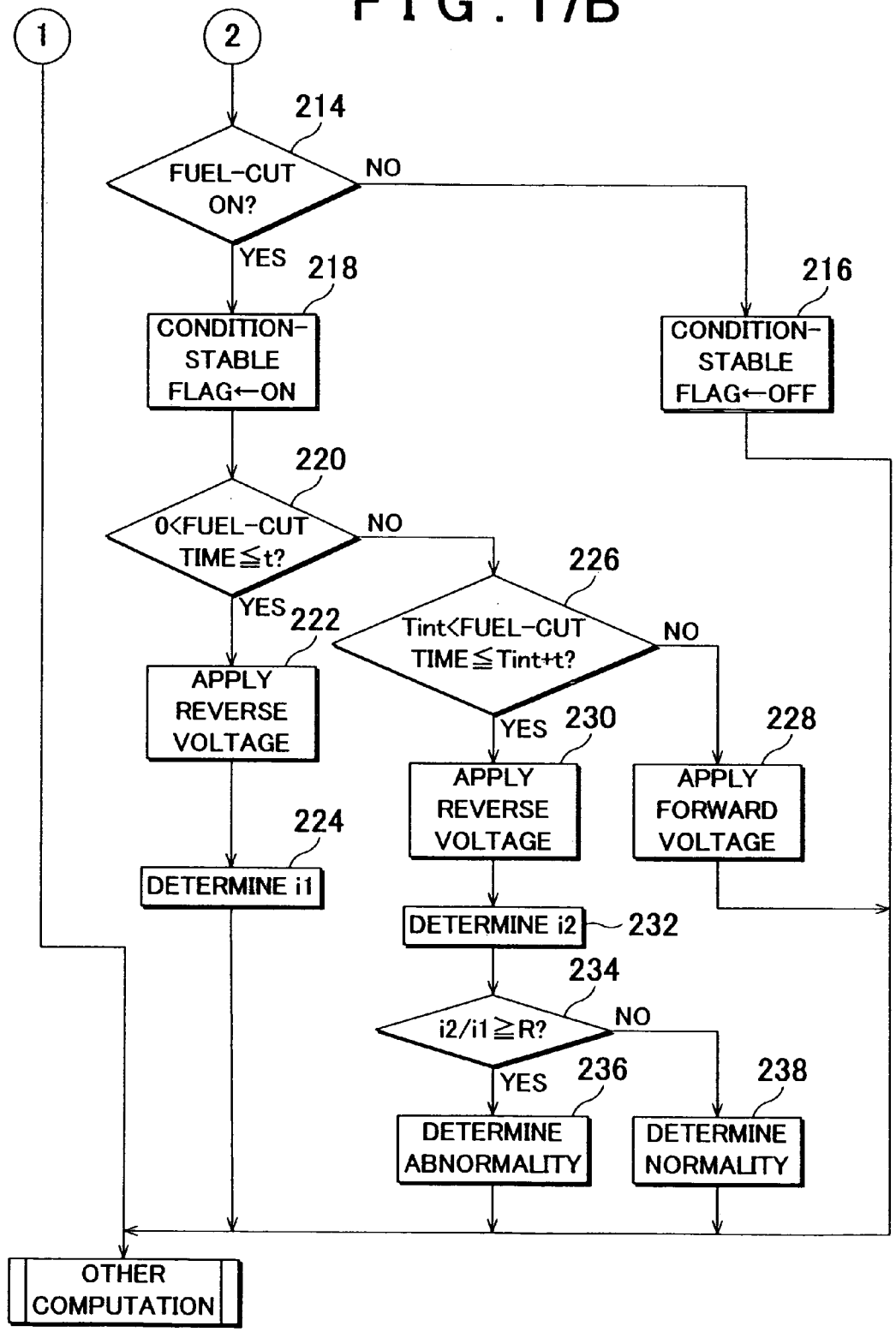

FIGS. 17A and 17B are flowcharts of a routine executed by the engine computer 30 in this embodiment. In the routine shown in FIGS. 17A and 17B, it is first distinguished whether or not the amount of intake air Ga has exceeded the criterion value G (step 190). It is determined that this condition is not satisfied, under a situation, for example, where after the internal combustion engine is started, the amount of intake air Ga is maintained at small value.

If it is recognized that Ga>G is not satisfied, the integrated amount of air GVOL is reset to "0" (step 192). Subsequently, it is distinguished whether or not a condition-hold flag is on (step 194). The condition-hold flag is set when the condition for detecting a sensor crack has held at the beginning of the fuel cut. Immediately after the internal combustion engine is started, this flag is off due to an initial process. In this case, it is distinguished at step 194 that the condition is not satisfied, and it is then distinguished whether or not a gas substitution flag is on (step 196).

The gas substitution flag is also turned off due to the initial process immediately after the internal combustion engine is started. Therefore, in this case, it is distinguished at step 196 that the condition is not satisfied. After this distinction is made, the delay time Tf is set to the maximum value (step 198). Then, the present process cycle promptly ends.

When the amount of intake air Ga becomes sufficiently large, it is determined at step 190 that Ga>G is satisfied. In this case, the integrated amount of air GVOL is then incremented (step 200). According to the process described above, the integrated amount of air GVOL can serve as a memory that stores the integrated amount of the amount of intake air Ga that occurs while Ga>G continuously holds.

Subsequently, it is distinguished whether or not the integrated amount of air GVOL has exceeded the criterion amount V (step 202). Immediately after Ga>G is satisfied, the relationship of GVOL>V does not hold, and therefore it is determined at step 202 that the condition is not satisfied. In this case, the gas substitution flag is turned off step 204, and then the present process cycle ends.

While the holding of Ga>G is maintained, the process of step 202 is executed every time the routine shown in FIGS. 17A and 17B is activated. If the amount of intake air Ga becomes less than G before GVOL>V is satisfied, steps 192 to 198 are executed, so that all the settings are returned to the initial state again. On the other hand, if the relationship of Ga>G is maintained until GVOL>V is satisfied, it is determined at step 202 that the condition is satisfied. In this case, the gas substitution flag is turned on (step 206), and then the delay time Tf is reset to "0" (step 208).

If the amount of intake air Ga becomes less than the criterion value G after the foregoing process, the process of steps 192 and 194 is executed, and subsequently at step 196 it is determined that the gas substitution flag is on. In this case, the delay time Tf is incremented (step 210), and then it is determined whether or not the delay time Tf is shorter than a criterion time Ts (step 212).

The delay time Tf is set to "0" (see the foregoing process of step 208) simultaneously with the turning on of the gas substitution flag. Therefore, Tf<Ts holds at the time point when the process of step 212 is executed for the first time. In this case, it is then determined whether or not the fuel-cut has been begun (step 214).

Until the beginning of the fuel-cut is recognized, it is determined at step 214 that the fuel-cut is off. In this case, the condition-hold flag is subsequently turned off (step 216), and then the present process cycle is ended.

As long as the amount of intake air Ga does not exceed the criterion value G, the process of step 214 is repeated in every process cycle of the routine shown in FIGS. 17A and 17B until the delay time Tf reaches the criterion time Ts. If the fuel-cut begins before the delay time Tf reaches the criterion time Ts, the condition of step 214 is satisfied, and therefore the condition-hold flag is turned on (step 218).

Next, it is distinguished whether or not the elapsed time following the time point of the beginning of the fuel-cut is less than or equal to the reverse voltage application time t (step 220).

The condition of step 220 holds immediately after the fuel-cut begins. In this case, a process of applying the reverse voltage to the air-fuel ratio sensor 10 is executed next (step 222). Subsequently, a process of acquiring the peak value of the reverse current as a first reverse current i1 is executed (step 224).

If the routine shown in FIGS. 17A and 17B is activated while the amount of intake air Ga remains less than the criterion value G, it is determined at step 194 in the present process cycle that the condition-hold flag is on. As a result, the process of step 214 and subsequent steps is unconditionally executed. Then, during the period from the beginning of the fuel-cut until the reverse voltage application time t elapses, the process of steps 220 to 224 is repeated.

If the reverse voltage application time t elapses while the fuel-cut is being executed, the condition of step 220 is not satisfied. In this case, it is next distinguished whether or not the elapsed time following the beginning of the fuel-cut is greater than the reverse voltage application interval Tint and less than or equal to a value Tint+t (step 226).

Until the elapsed time following the beginning of the fuel-cut reaches the reverse voltage application interval Tint, it is determined that the aforementioned distinction condition does not hold. In this case, a process of applying the forward voltage to the air-fuel ratio sensor 10 is next executed (step 228).

While the elapsed time has exceeded the reverse voltage application interval Tint but has not exceeded the value Tint+t, it is determined at step 226 that the condition holds. In this case, a process of applying the reverse voltage is first executed (step 230), and subsequently a process of acquiring the peak value of the reverse current as a second reverse current i2 is executed (step 232).

Until the elapsed time following the beginning of the fuel-cut exceeds the value Tint+t, the process of steps 230 and 232 is repeated every time the routine shown in FIGS. 17A and 17B is activated. As a result, the peak value of the reverse current occurring until the elapsed time reaches the value Tint+t is finally stored as a second reverse current i2.

In the routine shown in FIGS. 17A and 17B, subsequently to the process of step 232, it is distinguished whether or not the ratio (i2/i1) of the second reverse current i2 to the first reverse current i1 is greater than or equal to a criterion value R (step 234). The criterion value R is a value above 1.0, which is set in order to determine whether the absolute value of i2 is significantly larger than the absolute value of i1. Therefore, if the aforementioned condition holds, it can be determined that the absolute value of the second reverse current i2 is significantly larger than the absolute value of the first reverse current i1. In this case, the engine computer 30 recognizes the presence of a sensor crack, and makes an abnormality determination (step 236).

On the other hand, if at step 234 it is recognized that i2/i1≧R does not hold, it can be determined that the second reverse current i2 and the first reverse current i1 are not greatly different. In this case, the presence of a sensor crack is denied, and a normality determination is made (step 238).

When the elapsed time following the beginning of the fuel-cut exceeds Tint+t, it is determined at step 226 that the condition does not hold and then the process of step 228, that is, the process of applying the forward voltage to the air-fuel ratio sensor 10, is executed, every time the routine shown in FIGS. 12A and 12B is activated. When the fuel-cut ends afterwards, the condition of the step 214 fails to hold, and at step 216 the condition-hold flag is reset to the off-state.

After that, provided that the relationship of Ga>G is maintained, the process of step 210 (incrementing Tf) is repeated every time the routine shown in FIGS. 17A and 17B is activated. If as a result, the delay time Tf reaches the criterion time Ts, the condition of step 212 fails to hold, and the gas substitution flag is turned off (step 240). Through the above-described process, the initial state is restored.

According to the routine shown in FIGS. 17A and 17B, if the amount of intake air Ga becomes less than the criterion value G after the gas substitution flag is turned on (see step 206), the process of steps 194→196→210 to 216 is repeatedly executed until the fuel-cut begins, as described above. If the fuel-cut begins before the delay time Tf reaches the criterion time Ts, the sensor crack detecting process is performed by the process of steps 218 and subsequent steps.

Conversely, if the fuel-cut does not begin before the delay time Tf reaches the criterion time Ts, the process of step 240 is executed without execution of the sensor crack detecting process. As a result, the initial state is restored. That is, according to the process shown in FIGS. 17A and 17B, the sensor crack detection is permitted only when an environment that substantially assures that exhaust gas be sufficiently present in the atmosphere layer 18 is substantially complete at the time the fuel-cut is started. In the other cases, the detection is prohibited. Therefore, according to the system of this embodiment, it is possible to reliably avoid the inconvenience of a sensor crack being missed in detection if the throttle valve is gently closed.

In the meantime, in the foregoing description, the criterion time Ts is handled as a fixed value. However, the criterion time Ts may also be changed in accordance with the operation state of the internal combustion engine. That is, after the amount of intake air Ga becomes less than the criterion value G (after the throttle valve is closed), the scavenging of the interior of the atmosphere layer 18 progresses faster if the exhaust pressure is lower. Under a situation where the throttle valve is closed, the exhaust pressure is likely to be lower (negative pressure) if the engine rotation speed NE is higher. Therefore, the time during which sufficient exhaust gas remains in the atmosphere layer 18 is shorter if the engine rotation speed NE is higher.

Figure 18:
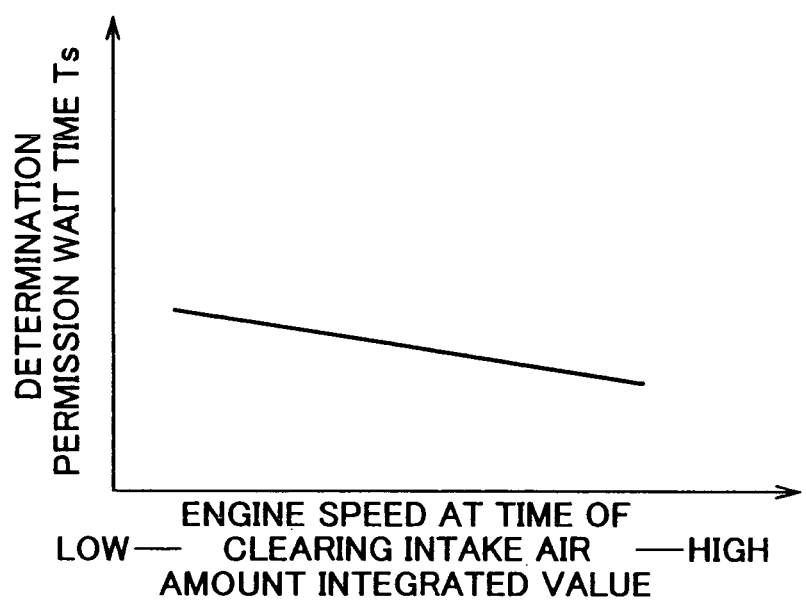
FIG. 18 is a map of the criterion time Ts used in a modification of the fifth embodiment.

FIG. 18 is an example of a map in which the criterion time Ts is determined in relation to the engine rotation speed NE on the basis of the aforementioned tendency. If this map is used, the engine computer 30 sets, for example, a criterion time Ts at the time point when the condition of step 190 fails to hold for the first time after the gas substitution flag is turned on. In this case, if the engine rotation speed NE is higher, the delay time Tf during which the sensor crack detection is permitted can be made shorter, and the determination accuracy regarding the presence/absence of a sensor crack can be further improved.

Furthermore, in the fifth embodiment, whether an environment for the entry of exhaust gas into the atmosphere layer 18 is substantially complete, and whether an environment for the scavenging of the atmosphere layer 18 is present are determined on the basis of the amount of intake air Ga. However, the determination technique is not limited to the foregoing technique. That is, the determinations may be carried out on the basis of the exhaust pressure.

In the fifth embodiment, the air-fuel ratio sensor 10 can be regarded as an "exhaust gas sensor" in the invention. Furthermore, functions of a "reverse voltage application device" and a "reverse current detection device" in the invention can be performed by the engine computer 30. Still further, the engine computer 30 can realize a "fuel-cut device" in the invention by performing the fuel-cut during deceleration, a "failure detection device" in the invention by executing the process of steps 218 to 238, an "exhaust pressure determination device" in the invention by executing the process of step 190, a "filling condition determination device" in the invention by executing the process of step 202, and a "filling condition maintenance device" and an "executing condition determination device" in the invention by executing the process of step 212.

Next, a sixth embodiment of the invention will be described with reference to FIGS. 18 to 24. The system of this embodiment can be realized in the hardware construction of the first embodiment by causing the engine computer 30 to execute a routine shown in FIGS. 24A and 24B, which will be described below.

Figure 19A:
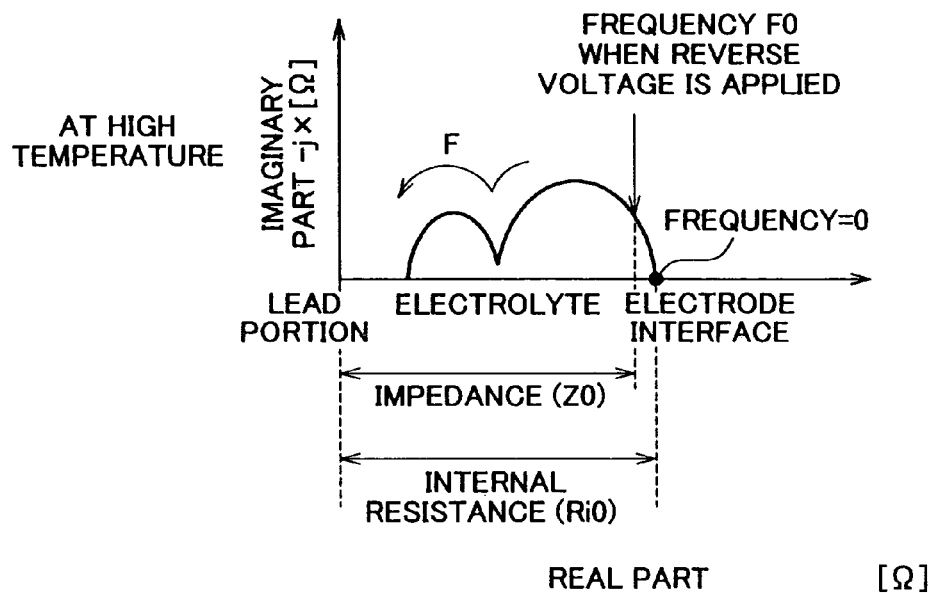
FIGS. 19A and 19B are diagrams for describing the temperature dependency of the impedance characteristic of the air-fuel ratio sensor.
Figure 19B:
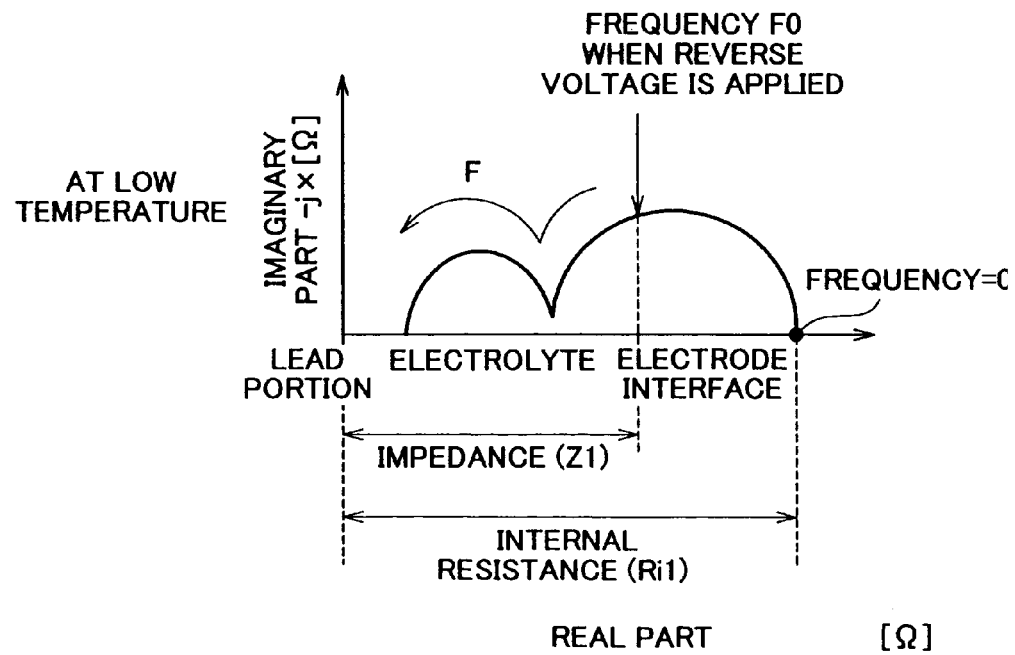

FIGS. 19A and 19B are diagrams for describing the temperature dependency of the impedance characteristic of the air-fuel ratio sensor 10. More specifically, FIG. 19A shows a frequency characteristic of the impedance in a state where the air-fuel ratio sensor 10 has been sufficiently warmed up (high-temperature condition). On the other hand, FIG. 19B shows a frequency characteristic of the impedance during the warming-up process (low-temperature condition). In these diagrams, the horizontal axis represents the real part of the impedance, and the vertical axis represents the imaginary part thereof.

The impedance of the air-fuel ratio sensor 10 has a frequency characteristic. In FIGS. 19A and 19B, the arrow F represents the axis of the frequency of the applied voltage. As shown in the diagrams, as the increases, the real component of the impedance of the air-fuel ratio sensor 10 decreases and the imaginary component thereof changes so as to exhibit two peaks, regardless of temperature. As is apparent from the comparison between FIG. 19A and FIG. 19B, the impedance shows a tendency in which the real component thereof increases for lower temperatures.

The system of this embodiment, as in the case of the second embodiment, measures the sensor current that occurs immediately following the application of the reverse voltage (the first reverse current i1) and the sensor current that occurs after the set time T (the second reverse current i2) during operation of the internal combustion engine. Then, on the basis of the electric current ratio i1/i2, the presence/absence of a sensor crack is determined (see FIGS. 7A and 7B). More specifically, if the electric current ratio (i1/i2) is greater than or equal to a criterion value Ic, the occurrence of a sensor crack is acknowledged.

Immediately after the reverse voltage is applied, a sharp change occurs in the applied voltage. In this case, the impedance of the air-fuel ratio sensor 10 assumes a value associated with the application of the alternating-current voltage. That is, the air-fuel ratio sensor 10 exhibits an impedance associated with the AC application, at the time of the measurement of the first reverse current i1. In contrast, after the set time T has elapsed, the applied voltage is stable. Therefore, at the time of the application of the second current, the air-fuel ratio sensor 10 exhibits an impedance associated with the direct-current application.

F0 shown in FIG. 19A is a frequency that is superposed on the applied voltage (reverse voltage) at the time of the measurement of the first reverse current i1. The air-fuel ratio sensor 10, after the end of warm-up, exhibits an "impedance Z0" in association with the frequency F0. In this case, the first reverse current i1 assumes a value that corresponds to Z0, regardless of the presence/absence of a sensor crack.

Furthermore, after the end of warm-up, the air-fuel ratio sensor 10 exhibits an internal resistance Ri0 in association with the application of the DC voltage (F=0) as shown in FIG. 19A. Therefore, if sufficient oxygen is present in the atmosphere layer 18, the second reverse current i2 assumes a value that corresponds to the internal resistance Ri0 of the air-fuel ratio sensor 10. On the other hand, if oxygen is not sufficiently present in the atmosphere layer 18, due to presence of a sensor crack, the second reverse current i2 assumes a value that is smaller than the value that corresponds to the internal resistance Ri0.

As shown in FIG. 19A, the impedance Z0 at the time of the measurement of the first reverse current i1 and the internal resistance Ri0 at the time of the measurement of the second reverse current i2 are substantially the same in the absolute magnitude. Therefore when a normal sensor has been sufficiently warmed up, the electric current ratio (i1/i2) is substantially equal to "1". On the other hand, when there is a sensor crack, i2 becomes smaller than the value it assumes during the normal state; therefore, the electric current ratio (i1/i2) becomes smaller than the value (approximately 1) assumed during the normal state. Hence, if the criterion value Ic is set between these two values, it is possible to detect a sensor crack.

However, when the temperature of the air-fuel ratio sensor 10 is low, a circumstance where a sensor crack cannot be detected with good accuracy by the foregoing technique occurs, as described below. That is, as shown in FIG. 19B, when the air-fuel ratio sensor 10 has low temperature, the impedance corresponding to the frequency F0 becomes Z1, and the impedance associated with the direct-current application becomes equal to the "internal resistance Ri1".

The magnitude of the impedance Z1 is not greatly different from the magnitude of the impedance Z0 occurring at high temperature. However, the internal resistance Ri1 at low temperature is remarkably greater than the internal resistance Ri0 that occurs at high temperature. If the internal resistance Ri1 is great, the sensor current cannot flow above the restrictions put by the internal resistance Ri1 even if a large amount of oxygen is present in the atmosphere layer 18. In other words, when the temperature is low, the sensor current is restricted by the internal resistance Ri1, that is, assumes a small value, regardless of the amount of oxygen in the atmosphere layer 18. Therefore, the second current at the time of low temperature is smaller than the first reverse current i1, no matter whether the sensor is normal or abnormal. As a result, the value of the electric current ratio (i1/i2) computed at the time of low temperature is greater than the normal value (approximately 1) regardless of the presence/absence of a sensor crack.

Figure 20:
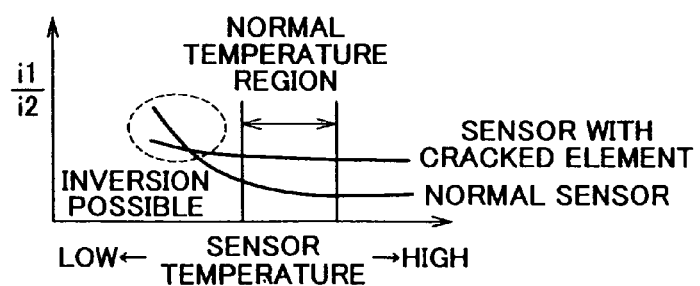
FIG. 20 is diagram representing a relationship between the electric current ratio (i1/i2) and the sensor temperature.

As described above, at the time of high temperature, the value of the electric current ratio (i1/i2) becomes great if a sensor crack occurs, and becomes small (approximately 1) if the sensor is normal. At the time of low temperature, the value of the electric current ratio (i1/i2) is greater than the normal value (approximately 1), regardless of the presence/absence of a sensor crack. FIG. 20 is a diagram in which this tendency is arranged and presented in a relationship between the electric current ratio (i1/i2) and the sensor temperature. That is, as shown in FIG. 20, the value of the electric current ratio (i1/i2) when the sensor is abnormal is greater than the normal value, in a region of the sensor temperature that is higher than a normal temperature region. On the other hand, the value of the electric current ratio (i1/i2) when the sensor is normal increases if the sensor temperature decreases. Therefore, in a low sensor temperature region, it is difficult to accurately detect the occurrence of a sensor crack on the basis of the electric current ratio (i1/i2).

Figure 21A:
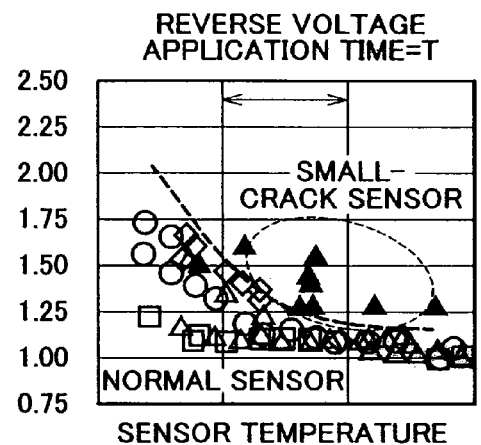
FIGS. 21A and 21B are diagrams for describing a relationship between the application time of the reverse voltage and the temperature characteristic of the electric current ratio (i1/i2)
Figure 21B:
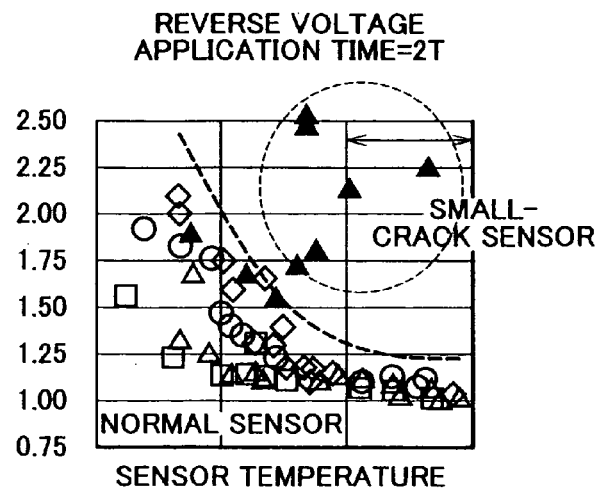

FIGS. 21A and 21B are diagrams for describing a relationship between the application time of the reverse voltage and the temperature characteristic of the electric current ratio (i1/i2). More specifically, FIG. 21A is a diagram obtained by plotting electric current ratios (i1/i2) actually measured with the reverse voltage application set time being T. FIG. 21B is a diagram obtained by plotting electric current ratio (i1/i2) actually measured with the reverse voltage application set time being 2T. In these diagrams, hollow marks Δ, □ and ○ represent results obtained by the air-fuel ratio sensor 10 that is normal. Solidified ▲, ■ and ● represent values obtained by the air-fuel ratio sensor 10 with a sensor crack.

Each of the characteristics shown in FIG. 21A and the characteristics shown in FIG. 21B overall match the characteristics shown in FIG. 20. That is, with regard to either of the two measurements, hollow-marked results (results obtained by a normal sensor) and solid-marked results (results obtained by an abnormal sensor) are separate from each other in a high temperature region whereas in a low temperature region, results of the hollow marks and results of the solid marks are mixed.

If the results shown in FIG. 21A and the results shown in FIG. 21B are compared further in detail, it can be seen that in a high temperature region, the results shown in FIG. 21B exhibit a clearer boundary between the results obtained by the normal sensor and the results obtained by the abnormal sensor than the results shown in FIG. 21A. However, the comparison in an intermediate temperature region shows that a boundary can be drawn between the results of the normal sensor and the results of the abnormal sensor in FIG. 21A whereas in FIG. 21B it is difficult to draw a boundary between the two groups of results.

That is, the results shown in FIGS. 21A and 21B indicate that long application time of the reverse voltage is preferable in order to improve the accuracy in the failure detection in a high temperature region whereas the application time of the reverse voltage needs to be shortened in order to enable the failure detection in an intermediate temperature region. Therefore, this embodiment is constructed so that in a low temperature region, execution of the failure detection is prohibited, and in an intermediate temperature region, the failure detection is performed with the reverse voltage application time being set at T, and in a high temperature region, the failure detection is performed with the time being set to T*n (n is, for example, 2).

Figure 22:
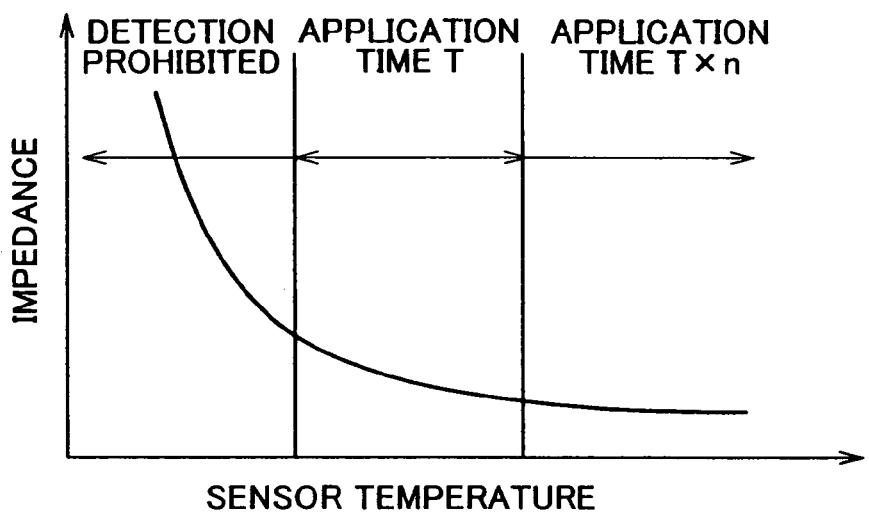
FIG. 22 is a diagram in which rules for execution of the failure detection are indicated by a relationship with the sensor temperature and a relationship with the impedance.

Incidentally, the sensor temperature of the air-fuel ratio sensor 10 has a correlation with the impedance thereof. Specifically, the relationship therebetween can be indicated by a characteristic curve as shown in FIG. 22. If this relation is known, rules regarding the execution of the above-described failure detection can be determined by the relationship with the impedance. Therefore, strictly speaking, in this embodiment, the determination regarding prohibition of the failure detection as well as the setting of the reverse voltage application time, and the like, are performed on the basis of the impedance of the air-fuel ratio sensor 10.

Figure 23:
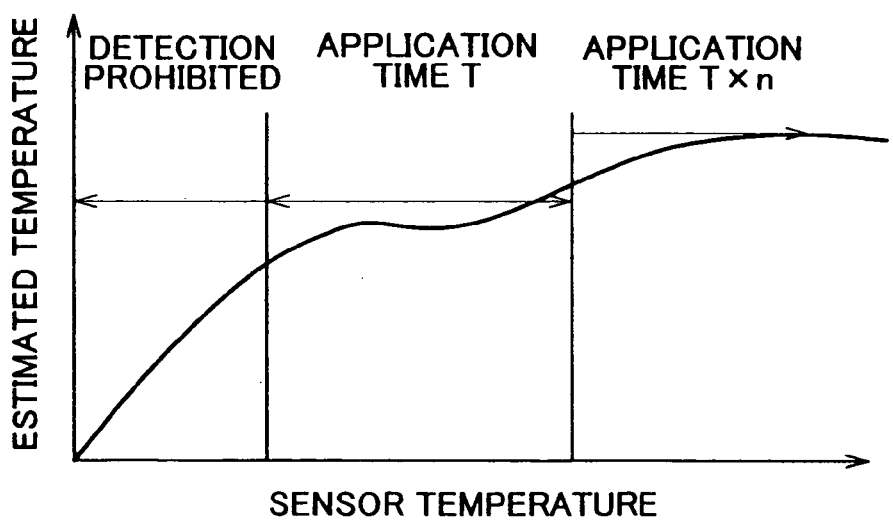
FIG. 23 is a diagram in which rules for execution of the failure detection are indicated by a relationship with the sensor temperature and a relationship with the estimated temperature of the sensor.

However, the physical quantity used as a basis for the determination regarding prohibition of the failure detection or the setting of the reverse voltage application time is not limited to the impedance. That is, the sensor temperature can be estimated on the basis of the accumulated amount of intake air following the startup of the internal combustion engine, the exhaust temperature, etc. Therefore, the region for prohibition of the failure detection, and the region where the application time should be set at T or T*n can be determined in relation to the estimated temperature as shown in FIG. 23. In this case, the determination regarding prohibition of the failure detection and the setting of the reverse voltage application time can be accomplished by using the estimated time as a basis.

Figure 24A:
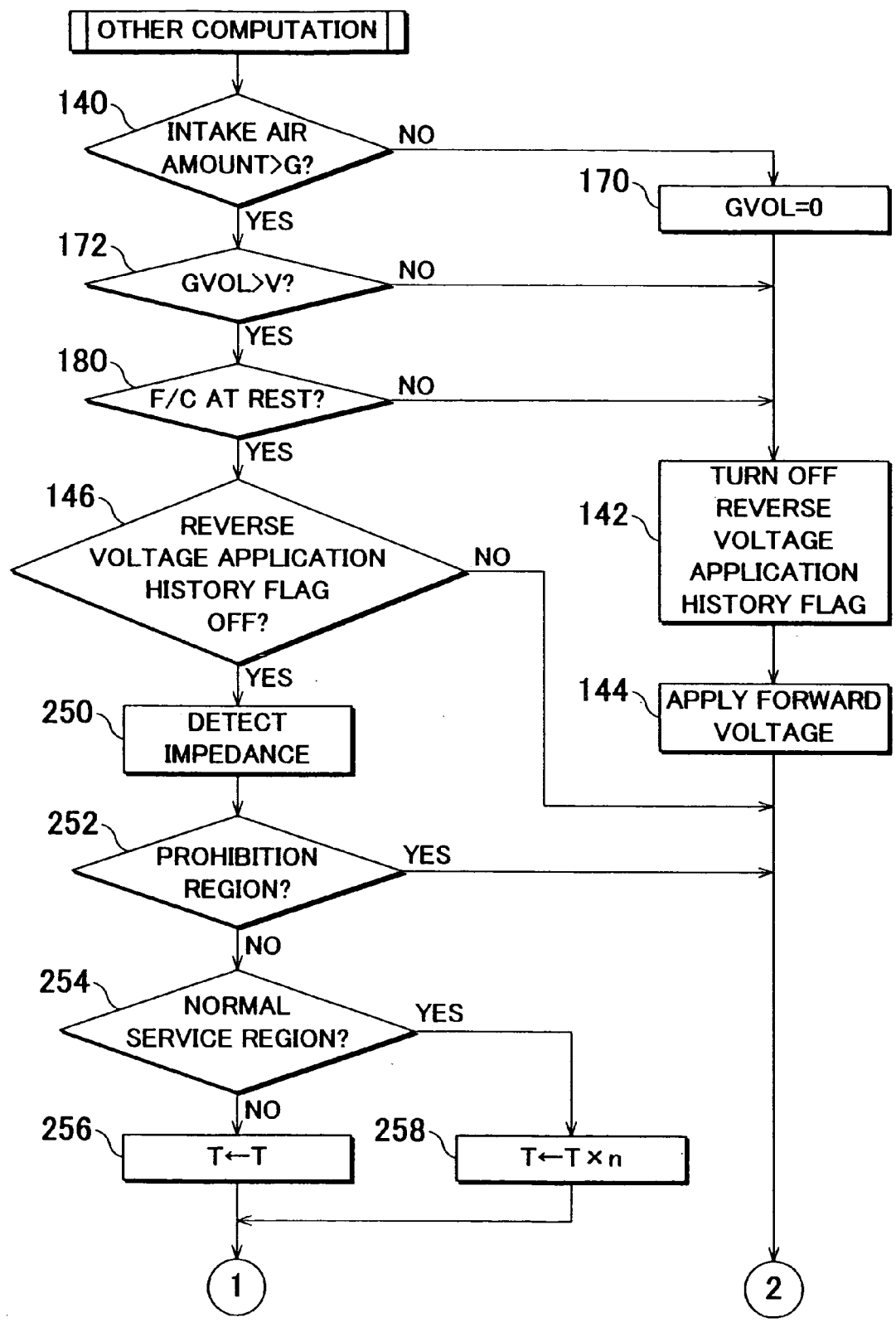
FIGS. 24A and 24B are flowcharts of a routine executed in a sixth embodiment of the invention.
Figure 24B:
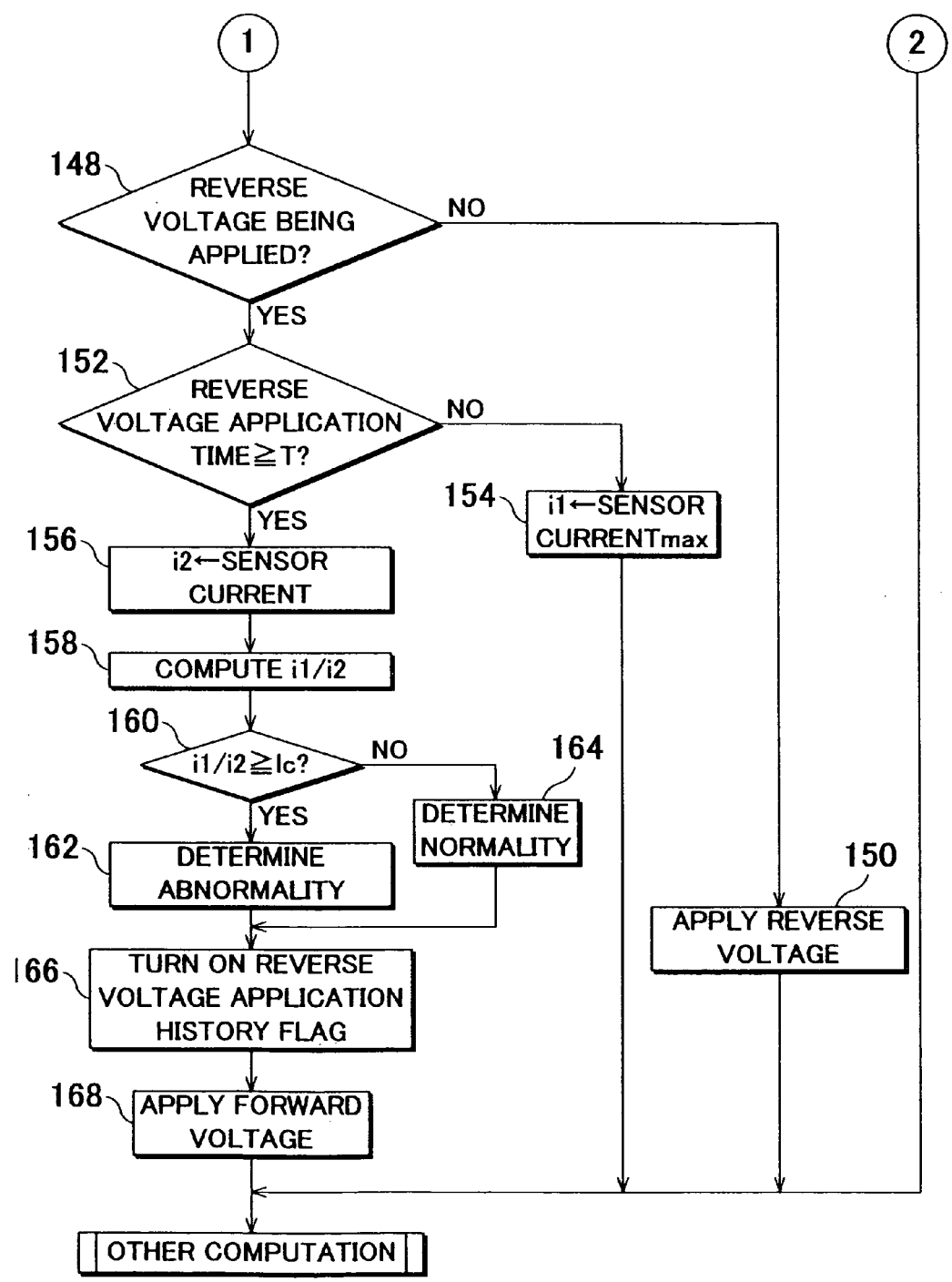

FIGS. 24A and 24B are flowcharts of a routine executed by the engine computer 30 in this embodiment. The routine shown in FIGS. 24A and 24B is substantially the same as the routine shown in FIG. 1, except that steps 250 to 258 are inserted between steps 146 and 148. The steps that are the same as those shown in FIGS. 12A and 12B are denoted by the same numerals in FIGS. 24A and 24B, and description thereof will be omitted or simplified below.

In the routine shown in FIGS. 24A and 24B, if the condition of step 146 is satisfied, the impedance of the air-fuel ratio sensor 10 is next detected (step 250). The impedance can be detected, for example, by providing a predetermined change in the applied voltage and then detecting the amount of change in the sensor current that occurs in association with the predetermined change. This technique for detection is known to public, and is not a main part of the invention, and therefore will not be further described herein.

Next, it is distinguished whether or not the detected impedance is within the region for prohibition of the failure detection (step 252). The engine computer stores a map in which the rules for the failure detection are determined in terms of the relationship with the impedance as shown in FIG. 22. In this embodiment, the aforementioned distinction is performed with reference to the map.

If it is distinguished that the impedance is within the region for the prohibition, then the present process cycle ends without further execution of the sensor crack detecting process. Therefore, according to the routine shown in FIGS. 24A and 24B, the execution of the abnormality determination in a low temperature region can be reliably prohibited.

On the other hand, if at step 252 it is distinguished that the impedance is not within the range for prohibition, it is then distinguished whether or not the impedance is within a normal service region (step 254). If it is distinguished that the impedance is not within the normal service region, it can be determined that the air-fuel ratio sensor 10 is still in the warming-up process, and is within an intermediate temperature region.

In order to detect a sensor crack in the intermediate temperature region, the application time of the reverse voltage needs to be short. Therefore, if the aforementioned distinction has been made, the set time T for the reverse voltage is set to a predetermined time T (step 256). After that, in steps 148 to 168, a process of detecting a sensor crack with the reverse voltage application time being set at T is executed.

If at step 254 it is determined that the impedance is within the normal service region, it can be determined that the warm-up of the air-fuel ratio sensor 10 has already been finished. In this case, the application time T of the reverse voltage is set to T*n (step 258). After that, in steps 148 to 169, the sensor crack detecting process is executed through the use of T*n.

As described above, according to the routine shown in FIGS. 24A and 24B, it is possible to determine whether or not to prohibit the failure detection or set the application time of the reverse voltage in accordance with the above-described rules. Therefore, according to the system of this embodiment, it is possible to reliably prevent false determination in the warm-up process, and to realize accurate failure detection in the intermediate temperature region, and to realize failure detection with very good accuracy in the normal service region (high temperature region).

Incidentally, although in the sixth embodiment, the technique for determining rules for the failure detection in accordance with the temperature of the air-fuel ratio sensor is combined with the technique of the fourth embodiment (see FIGS. 12A and 12B), the invention is not limited by this. That is, the foregoing technique may be combined with any one of the techniques of the first to third embodiments.

Furthermore, in the sixth embodiment, the application time of the reverse voltage is switched in accordance with the temperature region so as to enable the failure detection in the intermediate temperature region and obtain high detection accuracy in the high temperature region. However, this does not limit the invention. A reason why a lengthened time of the voltage application in the high temperature region is advantageous is that, in the region, an increased amount of oxygen pumping makes more conspicuous the difference between the value i2 when the sensor is normal and the value i2 when the sensor is abnormal. Then, the amount of oxygen pumping can also be increased by raising the applied voltage instead of lengthening the application time. Therefore, in the invention, the reverse voltage may be switched between different values so that the applied voltage in the high temperature region is greater than the applied voltage in the intermediate temperature region.

In addition, in the above-described sixth embodiment, the engine computer 30 can realize a "temperature acquisition device" in the invention by executing the process of step 250, and an "execution prohibition device" in the invention by executing the process of step 252. Furthermore, the engine computer 30 can realize a "stabilization time setting device" in the invention by executing the process of steps 256 and 258.

While the invention has been described with reference to preferred embodiments thereof, it is to be understood that the invention is not limited to the preferred embodiments or constructions. To the contrary, the invention is intended to cover various modifications and equivalent arrangements. In addition, while the various elements of the preferred embodiments are shown in various combinations and configurations, which are exemplary, other combinations and configurations, including more, less or only a signal element, are also within the spirit and scope of the invention.

What is claimed is:

1. A failure detection apparatus for an exhaust gas sensor that has
   an exhaust-side electrode exposed in an exhaust passage of an internal combustion engine,
   an atmosphere layer forming member that forms an atmosphere layer in an interior of the exhaust passage,
   an atmosphere-side electrode exposed to the atmosphere layer, and
   an electrolyte layer that is disposed between the exhaust-side electrode and the atmosphere-side electrode and that allows movement of oxygen ions between the exhaust-side electrode and the atmosphere-side electrode,
   the failure detection apparatus comprising:
   a reverse voltage application device that applies a reverse voltage between the atmosphere-side electrode and the exhaust-side electrode so that an electric potential of the exhaust-side electrode becomes higher than an electric potential of the atmosphere-side electrode;
   a reverse current detection device that detects a value of reverse current that flows between the atmosphere-side electrode and the exhaust-side electrode in association with application of the reverse voltage;
   an impedance correlation value acquisition device that acquires an impedance correlation value that has a correlation with an impedance between the atmosphere-side electrode and the exhaust-side electrode; and
   a failure detection portion that detects a failure of the exhaust gas sensor by comparing the value of reverse current and a criterion value while taking into account an influence of the impedance superposed on the value of reverse current.

2. The failure detection apparatus for the exhaust gas sensor according to claim 1, wherein the failure detection portion obtains a corrected reverse current by connecting the reverse current by the impedance correlation value, so that the influence of the impedance superposed on the value of reverse current is excluded, and detects failure in the exhaust gas sensor by comparing the corrected reverse current with the criterion value.

3. The failure detection apparatus for the exhaust gas sensor according to claim 1, wherein the failure detection portion obtains a corrected reverse current by correcting the value of reverse current by the impedance correlation value, so that the influence of the impedance superposed on the value of reverse current is excluded, and detects a failure in the exhaust gas sensor by comparing the corrected reverse current with the criterion value.

4. The failure detection apparatus for the exhaust gas sensor according to claim 1, wherein the failure detection portion obtains corrected criterion value by superposing on the criterion value the influence of the impedance superposed on the value of reverse current, and detects a failure in the exhaust gas sensor by comparing the value of reverse current and the corrected criterion value.

5. The failure detection apparatus for the exhaust gas sensor according to claim 1, wherein the failure detection portion detects a failure based on the value of reverse current detected after the reverse voltage has been applied for a predetermined time.

6. The failure detection apparatus for the exhaust gas sensor according to claim 5, wherein the impedance correlation value is the value of reverse current that occurs when the reverse voltage is applied.

7. The failure detection apparatus for the exhaust gas sensor according to claim 1, wherein the failure detection portion compares the value of reverse current detected after the reverse voltage has been applied for a predetermined time, with the criterion value.

8. The failure detection apparatus for the exhaust gas sensor according to claim 7, wherein the impedance correlation value is the value of reverse current that occurs when the reverse voltage is applied.

9. The failure detection apparatus for the exhaust gas sensor according to claim 1, wherein the impedance correlation value is the value of reverse current that occurs when the reverse voltage is applied.

10. The failure detection apparatus for the exhaust gas sensor according to claim 1, further comprising a forward voltage application device that applies a forward voltage between the exhaust-side electrode and the atmosphere-side electrode so that the electric potential of the exhaust-side electrode becomes higher than the electric potential of the atmosphere-side electrode, wherein the impedance correlation value is a value of the forward electric current that flows between the exhaust-side electrode and the atmosphere-side electrode when the voltage applied between the atmosphere-side electrode and the exhaust-side electrode is changed from the reverse voltage to the forward voltage.

11. The failure detection apparatus for the exhaust gas sensor according to claim 1, further comprising:

an exhaust pressure determination device that determines whether or not an exhaust pressure exceeds a reference value; and an execution condition determination device that permits detection of the failure only when a period during which the exhaust pressure exceeds the reference value exceeds a criterion period.

12. The failure detection apparatus for the exhaust gas sensor according to claim 1, further comprising:

a fuel-cut device that performs a fuel-cut if an engine speed reaches a permissible upper limit value; and an execution prohibition device that prohibits detection of the failure during execution of the fuel-cut.

13. The failure detection apparatus for the exhaust gas sensor according to claim 1, further comprising:

a temperature acquisition device that acquires a temperature of the exhaust gas sensor; and an execution prohibition device that prohibits detection of the failure if the temperature of the exhaust gas sensor has not reached an execution permission temperature.

14. The failure detection apparatus for the exhaust gas sensor according to claim 1, further comprising:

a temperature acquisition device that acquires a temperature of the exhaust gas sensor; and a predetermined time setting device that sets the predetermined time longer if the temperature of the exhaust gas sensor is higher.

15. A failure detection apparatus for an exhaust gas sensor that has an exhaust-side electrode exposed in an exhaust passage of an internal combustion engine, an atmosphere layer forming member that forms an atmosphere layer in an interior of the exhaust passage, an atmosphere-side electrode exposed to the atmosphere layer, and an electrolyte layer that is disposed between the exhaust-side electrode and the atmosphere-side electrode and that allows movement of oxygen ions between the exhaust-side electrode and the atmosphere-side electrode, the failure detection apparatus comprising:

a fuel-cut device that executes a fuel-cut when a fuel-cut condition is satisfied;

a reverse voltage application device that applies a reverse voltage between the atmosphere-side electrode and the exhaust-side electrode so that an electric potential of the exhaust-side electrode becomes higher than an electric potential of the atmosphere-side electrode;

a reverse current detection device that detects a value of reverse current that flows between the atmosphere-side electrode and the exhaust-side electrode in association with application of the reverse voltage;

a failure detection portion that detects the value of reverse current when the fuel-cut begins, and that detects the value of reverse current at a time point when the fuel-cut has continued for a predetermined time, and that detects a failure in the exhaust gas sensor based on those values of reverse current;

an exhaust pressure determination device that determines whether or not an exhaust pressure exceeds a reference value;

a filling condition determination device that determines that an exhaust gas filling condition is satisfied if a period during which the exhaust pressure exceeds the reference value exceeds a criterion period;

a filling condition maintenance device that maintains holding of the exhaust gas filling condition only during a period that begins after the exhaust pressure becomes lower than the reference value and that ends when a filling maintenance time elapses; and an execution condition determination device that permits detection of the failure only if the holding of the filling condition is recognized at a time point when the fuel-cut begins.

16. A failure detection method for an exhaust gas sensor that has
- an exhaust-side electrode exposed in an exhaust passage of an internal combustion engine,
- an atmosphere layer forming member that forms an atmosphere layer in an interior of the exhaust passage,
- an atmosphere-side electrode exposed to the atmosphere layer, and
- an electrolyte layer that is disposed between the exhaust-side electrode and the atmosphere-side electrode and that allows movement of oxygen ions between the exhaust-side electrode and the atmosphere-side electrode, the failure detection method comprising:
- applying a reverse voltage between the atmosphere-side electrode and the exhaust-side electrode so that an electric potential of the exhaust-side electrode becomes higher than an electric potential of the atmosphere-side electrode;
- detecting a value of reverse current that flows between the atmosphere-side electrode and the exhaust-side electrode in association with application of the reverse voltage;
- acquiring an impedance correlation value that has a correlation with an impedance between the atmosphere-side electrode and the exhaust-side electrode; and
- detecting a failure of the exhaust gas sensor by comparing the value of reverse current and a criterion value while taking into account an influence of the impedance superposed on the value of reverse current.

17. A failure detection method for an exhaust gas sensor that has
- an exhaust-side electrode exposed in an exhaust passage of an internal combustion engine,
- an atmosphere layer forming member that forms an atmosphere layer in an interior of the exhaust passage,
- an atmosphere-side electrode exposed to the atmosphere layer, and
- an electrolyte layer that is disposed between the exhaust-side electrode and the atmosphere-side electrode and that allows movement of oxygen ions between the exhaust-side electrode and the atmosphere-side electrode, the failure detection method comprising:
- executing a fuel-cut when a fuel-cut condition is satisfied;
- applying a reverse voltage between the atmosphere-side electrode and the exhaust-side electrode so that an electric potential of the exhaust-side electrode becomes higher than an electric potential of the atmosphere-side electrode;
- detecting a value of reverse current that flows between the atmosphere-side electrode and the exhaust-side electrode in association with application of the reverse voltage;
- detecting a first value of reverse current when the fuel-cut begins, and detecting a second value of reverse current when the fuel-cut has continued for a predetermined time, and detecting a failure in the exhaust gas sensor based on the first and second detected values of the reverse current;
- determining whether or not an exhaust pressure exceeds a reference value;
- determining that an exhaust gas filling condition is satisfied if a period during which the exhaust pressure exceeds the reference value exceeds a criterion period;
- maintaining holding of the exhaust gas filling condition only during a period that begins after the exhaust pressure becomes lower than the reference value and that ends when a filling maintenance time elapses; and
- permitting detection of the failure only if the holding of the filling condition is recognized at a time point when the fuel-cut begins.

* * * * *